(12) United States Patent
Breslauer et al.

(10) Patent No.: US 10,100,350 B2
(45) Date of Patent: Oct. 16, 2018

(54) MOLECULAR CONSTRUCTS FOR DIFFERENTIATING A TARGET MOLECULE FROM AN OFF-TARGET MOLECULE

(75) Inventors: Kenneth J. Breslauer, Edison, NJ (US); William H. Braunlin, New York, NY (US); Leslie C. Beadling, Wilmington, DE (US); Jens Volker, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 433 days.

(21) Appl. No.: 14/110,618

(22) PCT Filed: May 7, 2012

(86) PCT No.: PCT/US2012/036816
§ 371 (c)(1),
(2), (4) Date: Jun. 4, 2014

(87) PCT Pub. No.: WO2012/154689
PCT Pub. Date: Nov. 15, 2012

(65) Prior Publication Data
US 2014/0303015 A1 Oct. 9, 2014

Related U.S. Application Data

(60) Provisional application No. 61/483,323, filed on May 6, 2011.

(51) Int. Cl.
C12Q 1/68 (2018.01)
*C12Q 1/6837* (2018.01)
*C12Q 1/6811* (2018.01)
*C12Q 1/6825* (2018.01)
*C12Q 1/6832* (2018.01)

(52) U.S. Cl.
CPC .......... *C12Q 1/6837* (2013.01); *C12Q 1/6811* (2013.01); *C12Q 1/6825* (2013.01); *C12Q 1/6832* (2013.01)

(58) Field of Classification Search
None
See application file for complete search history.

(56) References Cited

U.S. PATENT DOCUMENTS

| | | | |
|---|---|---|---|
| 6,815,163 B1 | 11/2004 | Breslauer et al. | |
| 2003/0096242 A1* | 5/2003 | Keys ................ | C12Q 1/6818 435/6.11 |
| 2005/0176032 A1 | 8/2005 | Breslauer et al. | |
| 2007/0243534 A1* | 10/2007 | Seul ................ | C12Q 1/6818 435/6.11 |
| 2010/0204461 A1 | 8/2010 | Beadling et al. | |

OTHER PUBLICATIONS

Trapp et al. (2011) "Stability of double-stranded oligonucleotide DNA with a bulged loop: a microarray study." BMC Biophysics 4:20.*

(Continued)

*Primary Examiner* — Karen S. Weiler
(74) *Attorney, Agent, or Firm* — Robert C. Netter, Jr.; Dann, Dorfman, Herrell & Skillman

(57) ABSTRACT

Molecular constructs, populations thereof, arrays, compositions, methods and kits for differentiating a target molecule from an off-target molecule are provided.

19 Claims, 12 Drawing Sheets

Specification includes a Sequence Listing.

(56) References Cited

OTHER PUBLICATIONS

Vallee-Belisle, A., et al., "Engineering Biosensors with Extended, Narrowed, or Arbitrarily Edited Dynamic Range" J. Amer. Chem. Soc. (2012) 134:2876-2879.
Manoor, M.S., et al., "Nanogap Dielectric Spectroscopy for Aptamer-Based Protein Detection" Biophys. J. (2010) 98:724-732.
Braulin, W.H., et al., "Conformational Screening of Oligonucleotides by Variable Temperature High Performance Liquid Chromatography: Dissecting the Duplex-Hairpin—Coil Equilibria of d(CGCGAATTCGCG)" Biopolymers (2004) 74:221-231.
Volker, J., et al., "Energy Crosstalk between DNA Lesions: Implications for Allosteric Coupling of DNA Repair and Triplet Repeat Expansion Pathways" J. Am. Chem. Soc. (2010) 132:4095-4097.
Gelfand, C.A., et al. "A quantitative method for evaluating the stabilities of nucleic acids" Proc. Natl. Acad. Sci. (1999) 96:6113-6118.
Bishop, J., et al., "Competitive Displacement of DNA during Surface Hybridization" Biophys J. (2007) 92:L10-L12.
Plum, G.E., et al., "Fluorescence Energy Transfer Monitored Competitive Equilibria of Nucleic Acids: Applications in Thermodynamics and Screening" Biopoly. (2002) 61:214-223.
Mir, et al. "Towards a Target label-free suboptimum oligonucleotide displacement-based detection system." Anal. Bioanal Chem. May 3, 2008;391:2145-2152.
Han, et al. "Design strategies for aptamer-based biosensors." Sensors. May 4, 2010;10:4541-4557.

\* cited by examiner 100 fM PQT1

10 pM PQC3

100 pM PQC8

10 nM PQT1

MOLECULAR CONSTRUCTS FOR DIFFERENTIATING A TARGET MOLECULE FROM AN OFF-TARGET MOLECULE

This application is a § 371 application of PCT/US2012/036816, filed May 7, 2012, which claims priority under 35 U.S.C. § 119(e) to U.S. Provisional Patent Application No. 61/483,323, filed May 6, 2011. The foregoing applications are incorporated by reference herein.

This invention was made with government support under Grant No. R43-AI074089 awarded by the National Institutes of Health/National Cancer Institute and Grant No. R43-GM078946 awarded by National Institutes of Health/National Cancer Institute. The government has certain rights in the invention.

FIELD OF THE INVENTION

The present invention relates to differentiating a target molecule from an off-target molecule, the target molecule having a target domain and the off-target molecule having an off-target domain that differs from said target domain.

SUMMARY OF THE INVENTION

In accordance with the present invention, a molecular construct (or complex) for differentiating a target molecule from an off-target molecule is provided in which the target molecule has a target domain and the off-target molecule has an off-target domain that differs from said target domain. Such a molecular construct comprises a. a first domain that is capable of binding to said target domain, and b. a second domain that is at least partially hybridizable with said first domain, wherein said first domain is capable of binding to said off-target domain, wherein a hybrid of said first domain with said second domain is i. in a state of predetermined stable equilibrium in the absence of said target domain and ii. in a state of predetermined metastable equilibrium in the presence of said target domain; and wherein the free energy of displacement of said second domain by said target domain from said hybrid of said first domain with said second domain is energetically more favored than the free energy of displacement of said second domain by said off-target domain from said hybrid of said first domain with said second domain.

In the molecular construct of the present invention, the off-target domain may also be generally homologous with respect to the target domain. Further, in the molecular construct of the present invention, the off-target domain may also differ from the target domain either chemically by at least one functional group or conformationally or both. Further, in accordance with the present invention, a population of such molecular constructs (or probe complexes) may be provided. Such a population may comprise a. a first subpopulation of at least one said molecular construct with respect to a first target domain and b. a second subpopulation of at least one said molecular construct with respect to a second target domain, wherein said first target domain differs from said second target domain. In another embodiment, the population comprises a. a first subpopulation comprising at least one said molecular construct with respect to a first off-target domain and b. a second subpopulation comprising at least one said molecular construct with respect to a second off-target domain, wherein said first off-target domain differs from said second off-target domain.

In accordance with another aspect of the instant invention, arrays are provided. In a particular embodiment, the arrays comprise at least one biosensor element on a solid support. Each biosensor element may comprise at least one molecular construct (or probe complex) of the instant invention. In a particular embodiment, the array comprises a plurality of populations of molecular constructs of the instant invention for 1) detecting a plurality of different target molecules in a sample and/or 2) determining the relative number of target molecules in a sample, wherein the free energy of displacement of each of those populations differs with respect to each other of those populations so as to be capable of 1) identifying different target molecules in the sample and/or 2) determining the relative number of target molecules of a population from another population in said sample. In a particular embodiment, the array comprises a plurality of populations of molecular constructs of the instant invention for identifying a plurality of different target molecules in a sample and determining the relative number of each of those different target molecules in the sample, wherein the free energy of displacement of each of those populations differs with respect to each other of those populations so as to be capable of identifying each different target molecule in the sample and the free energy of displacement of each of those populations differs with respect to each other of those populations so as to be capable of determining the relative number of each of those different target molecules of a population from another population in the sample. In a particular embodiment, the number of different targets is from about 2 to 1000 or more, about 2 to about 10, about 2 to about 100, about 100 to about 1000, or greater than 1000. In a particular embodiment, the ratio of the free energy of displacement of one population to another population is about 1.1, greater than about 1.1, about 1.1 to about 1.2, 1.5, or 2.0, about 1.2 to about 1.5, about 1.5 to about 2.0, or greater than 2.0. Kits comprising the arrays of the instant invention are also provided.

In accordance with another aspect of the instant invention, methods for differentiating a target molecule from an off-target molecule are provided. The method may be used to detect and/or quantitate a nucleic acid sequence of interest or target molecule. In a particular embodiment, the method comprises contacting at least one molecular construct (or probe complex) of the instant invention with a sample (e.g., a biological sample). In a particular embodiment, the method comprises a) contacting a population of probe complexes (or molecule constructs) with a sample, and b) detecting the formation of complexes between the probe strand and a nucleic acid molecule from the sample, wherein the presence of such complexes is indicative of the presence and or quantity of the nucleic acid sequence of interest. The population of probe complexes may comprise at least i) a first subpopulation of probe complexes comprising a probe strand and a competitor strand, wherein the competitor strand comprises at least one hybridization domain (particularly at least two) and at least one domain which does not hybridize with the probe strand, wherein the hybridization domain is at least partially complementary to the probe strand, and ii) a second subpopulation of probe complexes comprising a probe strand and a competitor strand, wherein the competitor strand comprises at least one hybridization domain (particularly at least two) and at least one domain which does not hybridize with the probe strand, wherein the hybridization domain is at least partially complementary of the probe strand, wherein the non-hybridization domain of the second subpopulation differs from the non-hybridization domain of the first subpopulation. In a particular embodiment, the probe and competitor strands are reversed.

BRIEF DESCRIPTION OF THE DRAWING

FIG. 4 provides simulations of the target binding behavior of competitive surface probes.

FIG. 5A is a simulation under typical solution conditions with 0.1 μM MecA probe, 100 mM KCl, 1 mM $MgCl_2$. FIG. 5B provides a simulation under conditions mimicking those on a surface, where the probe concentration is negligible compared to the target. For FIG. 5A, half-saturation of probe occurs at $5 \times 10^{-8}$ M target, corresponding to a critical cycle number of 26. For FIG. 5B, half-saturation occurs when the concentrations of the perfect hybrid and the single mismatch are $8 \times 10^{-12}$ and $4 \times 10^{-10}$ M, respectively, corresponding to critical cycle numbers of 13 and 19.

DETAILED DESCRIPTION OF THE INVENTION

Figure 1A:
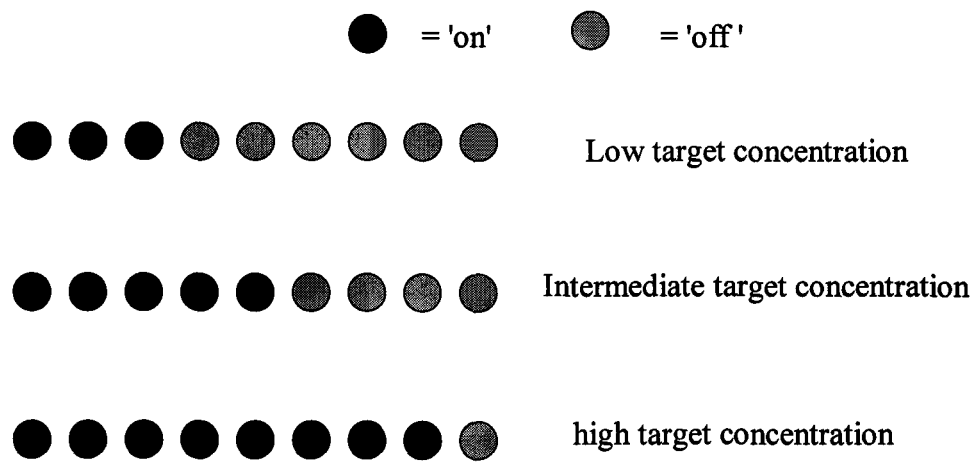
FIG. 1A provides a schematic of the principle of action of Quantitative Recognition Arrays (DNA-meter and Aptameter).

In accordance with the instant invention, energetically tunable probes are provided. Watson-Crick, canonical G•C and A•T pairing interactions represent the molecular language/code by which two complementary DNA sequence domains selectively recognize and bind/hybridize to one another. This selective recognition pattern has been employed to design specific DNA sequences which can probe for the presence of complementary target DNA domains. Applications of such probe-target hybridization assays have been extensive; including testing (probing) for the presence of a particular target gene, gene transcript, secondary structural element, or functional/regulatory sequence domain; creating a priming duplex domain for PCR or sequencing methods; modulating the activity of a nucleic acid construct; etc. More recently, probe-target hybridization assays, including variants, as elaborated below, have been used to: map actively transcribed genes in entire cell lines (the so called transcriptome), as well as in different tissue types, in systems biology applications, and to identify genetic changes in cancerous tissues.

Simple hybridization between single stranded probes and single stranded targets often lacks the requisite selectivity, with secondary and tertiary probe-target "hits" and "misses" compromising many applications. Accordingly, greater stringency is required than what has been afforded by simple hybridization. This realization led to the design of a number of hybridization assays predicated on strand invasion, strand displacement, or strand exchange strategies in which either the probe or the target, or both, were in a duplex or other pre-organized state. For example, the probe may be in the duplex state and a successful target hit requires strand displacement. Using such an approach, one could directly detect subtle differential stabilities between one target and another, rather than having to distinguish small differences between two large numbers derived from independent measurements. While an improvement over traditional single stranded probe/single stranded target assays, such direct differential approaches still required subtle tuning of the relative stabilities of probes and targets to achieve the stringency required in many applications. To this end, efforts focused on designing into the probe specific mismatches, modified bases, and even non-nucleoside components to achieve greater selectivity for the assay such that the duplex probe comprises a mismatch or non-Watson-Crick imperfection. However, such "tuning" of the differential energetics often also tampered with the underlying Watson-Crick recognition code, thereby adding an additional layer of complexity and, at times, ambiguity, to the resulting interpretation of the "hit" (successful hybridization). As a result, even these second generation hybridization assays frequently exhibited unacceptable levels of false positives and false negatives.

Specificity is defined as the difference ($\Delta\Delta G$) of the binding free energy ($\Delta G$) of probe to a specific target and probe binding to an off-target. Stringency can then be defined as the relative contribution of binding selectivity to the overall binding free energy of probe to target. Stringent conditions are those where binding to the specific target is stable, but where binding to the non-specific target is not. Seen in this light, it is clear that if affinity can be attenuated while maintaining constant selectivity, then stringency will necessarily be enhanced and can be optimized. Selectivity refers to the ability of the probe to distinguish and preferentially recognize/bind a specific target from among an ensemble of (closely related) off-targets. Selectivity may, in looser terms, also be considered as the ability of a ligand to interact with a particular population of target molecules in preference to others. The term selectivity may in some cases be used to imply a degree of specificity. In the limit of one off-target, the definition of specificity and selectivity are identical.

With duplex hybridization, probe binding to non-specific target differing by a single mismatch compared to a specific target is correlated with a free energy difference of only a few kcal per mole, roughly independent of salt and temperature. Under high salt and low temperature conditions, the hybridization of two strands to form a duplex is so strongly favored, that mismatches are often well tolerated, and the ability to discriminate between specific and non-specific targets will be compromised. In order to discriminate between mismatch and a match target directly it is better to work under low salt and/or higher temperature conditions where the overall hybridization free energy is reduced and stringency is enhanced. Under these circumstances the difference of a few kcal per mole between probe binding to specific and non-specific targets becomes significant compared to the total free energy of hybridization, and can be readily measured. Under conditions where melting occurs, the overall hybridization free energy approaches zero, thereby enhancing the ability to monitor differences in free energy due to mismatches or other defects.

Temperature is a very useful and well recognized parameter for enhancing stringency (i.e. the contribution of binding selectivity to the overall probe-target binding free energy). Less well appreciated, but likewise useful, is the concept of modulating binding affinity (e.g., strength of an interaction between two entities, Ka) through competitive interactions.

One very useful actualization of this principle is found in competitive probe technology (Gelfand et al. (1999) Proc. Natl. Acad. Sci., 96:6113-8; Plum et al. (2001) Biopolymers 61:214-23; U.S. Pat. No. 6,815,163). Competitive probe technology allows the measurements of small differences in free energy between the hybridization of two different target molecules to the same probe molecule. The reference duplex AD is formed from a fluorescent acceptor labeled probe A and a donor labeled target D. Competition with an unlabeled strand X results in the formation of competitor/acceptor duplex and a decrease in FRET. Such competitive constructs are capable of distinguishing free energy differences as small as 1 kcal per mol, and can thereby be used to distinguish SNPs and a variety of small-scale defects, even in the presence of a very stable duplex. Another significant advantage of competitive probes is that they can be designed and optimized to avoid kinetic traps that are a significant concern for molecular beacons and other hairpin probes, particularly at lower temperatures (Braunlin et al. (2004) Biopolymers 74:221-31).

It is shown herein that one can selectively tune the energetics of a duplex or pre-engaged probe without altering the canonical Watson-Crick recognition code of the component probe strand used to seek out (hybridize to) a complementary target domain. Using this strategy, one is able to enhance stringency without compromising target identification. Here it is demonstrated that this goal can be achieved in one manifestation by initially complexing or "tying up" a probe strand with a complementary competitor strand (also referred to metaphorically here as a "masking tape" strand) in which the competitor strand element used to modulate the stability of the overall probe complex (or molecular construct) (and therefore the "availability" of the probe strand to bind target) is extra-helical and does not alter the Watson-Crick recognition interface of the probe. In a particular embodiment, the strength (stability) of the resulting probe complex (or molecular construct) is modulated by changing the size and/or sequence of a non-hybridizing domain, such as a bulge or loop, within the non-probing, "masking tape" strand. As such, there is no requirement for one to alter the Watson-Crick recognition code of the probe strand. The significant feature in such constructs is that one is able to tune the energetics of the probe-competitor complex, and therefore the availability of the probe strand to hybridize to its complement target, as a function of target concentration, without altering the recognition elements of the probe for the target. This represents a qualitative and quantitative advance relative to duplex probe approaches which require less refined and predictable tuning via alterations in probe components essential for selective target recognition.

Using such molecular constructs (complexes), it is shown herein that the probe strand in complex with the most destabilizing masking tape strand is selectively displaced from the probe complex at low target strand concentration to form the probe-target complex that defines a successful hit. Only at sequentially higher target concentrations are the more stable masking tape strands displaced from the probe, in precisely the order that maps with the relative stabilities of the initial probe complexes. Such bulge or loop families of energetically discrete probe complexes may be referred to as "tuning fork" probes. It is demonstrated that such tunable probe complexes not only can selectively detect the presence of target sequences, but also can quantitate the amount of target present. This aggregate capacity allows for the referral to the methodology described here as a DNAmeter. However, the instant invention is not limited to DNA. Indeed, the competitor-probe complex and target-probe complex may be complexes of any nucleic acid molecules (e.g., DNA, RNA, and nucleic acid analogs or mimics (inclusive of locked nucleic acids, PNAs, and other base or backbone modifications)) or other specific binding pair including proteins and polypeptides.

For simplicity, the following description generally details the use of nucleic acid molecules. However, as stated above, the instant invention encompasses the use of any specific binding pair.

According to one aspect of the instant invention, the complexes comprise nucleic acid molecules. In a particular embodiment, the competitor strand comprises at least one, particularly two or more regions, which specifically hybridize with the probe strand and one or more other regions (e.g., a bulge or loop region) which do not hybridize with the probe strand. In a particular embodiment, the competitor strand may comprise a single non-hybridizing domain between two hybridizing domains or the competitor strand may comprise two non-hybridizing domains interspersed among three hybridizing domains, etc.

The non-hybridizing domain(s) may be of any length. In a particular embodiment, the non-hybridizing (e.g., loop) domain comprises from 1 to about 50 nucleotides, particularly from 1 to about 25 nucleotides. The sequence of the non-hybridizing domain does not specifically hybridize with the probe, particularly under the assay conditions employed. For example, the sequence of the non-hybridizing domain may have less than 50% identity, less than 40% identity, less than 30% identity, or less than 25% identity with the probe sequence. In a particular embodiment, the nucleotides of the non-hybridizing domain are the same (e.g., all thymidines). Alternatively, the sequence of the non-hybridizing domain is variable.

The domains which specifically hybridize with the probe strand may be at least complementary, particularly completely complementary, to the probe strand and/or target strand. In other words, the sequence of the two or more hybridizing domains when considered in tandem as a single sequence create a sequence that is complementary, particularly completely complementary, to the probe and/or target strand. The hybridizing domain(s) may be of any length. In a particular embodiment, the hybridizing domain comprises from 1 to about 50 nucleotides, from 1 to about 25 nucleotides, or from about 10 to about 25 nucleotides. Notably, the competitor strand need not be completely complementary for the entire length of the probe strand (or target strand). Indeed, the probe, competitor and target need not be the same length (and typically will not be).

In a particular embodiment, a molecular construct with a single hybridizable domain (at least partially complementary) and a single non-hybridizable domain effect for modulating binding to the probe strand might be formed with these domains at least partially overlapping in sequence space and the non-hybridizable domain forming a secondary structure on its own, i.e, for example, a probe that contains a number of cytosines at either 5' or 3' terminus, in which case the hybridizable part of the competitor strand contains complimentary guanines. If the non-hybridizable domain is also rich in guanines, these could fold up together with the guanines in the hybridizable domain to form a G tetraplex in competition to binding to the probe strand, thereby modulating the interactions with the probe strand. In other words—the non-hybridizable domain forms a self structure with part of the hybridizable domain in competition to binding to the probe strand (and that would almost make it a nested arrangement). In a particular embodiment, the hybridizable domain and the non-hybridizable domain do not necessarily correspond to clearly distinct regions in (linear) sequence space, but they could partially overlap.

The instant invention also encompasses populations of probe-competitor complexes. The population of probe-competitor complexes may comprise at least one subpopulation. In a particular embodiment, each subpopulation differs from other subpopulations by having a different non-hybridizing domain. For example, a population of the instant invention may comprise a first subpopulation having a non-hybridizing domain comprising a loop of X nucleotides, a second subpopulation having a non-hybridizing domain comprising a loop of X+Y (e.g., 1) nucleotides, and so on. In a particular embodiment, the population comprises a "ladder" of subpopulations wherein the length of the loop domain is incrementally increased. The population of probe-competitor complexes may be in solution or spatially confined (e.g., attached to a solid support). When attached to a solid support, the subpopulations may be attached in an ordered or array format to the solid support.

In accordance with the present invention, a molecular construct for differentiating a target molecule from an off-target molecule may be provided in which the target molecule has a target domain and the off-target molecule has an off-target domain that differs from said target domain. Such a molecular construct comprises a. a first domain that is capable of binding to said target domain, and b. a second domain that is at least partially hybridizable with said first domain, wherein said first domain is capable of binding to said off-target domain; wherein a hybrid of said first domain with said second domain is i. in a state of predetermined stable equilibrium in the absence of said target domain and ii. in a state of predetermined metastable equilibrium in the presence of said target domain; and wherein i. the free energy of displacement of said second domain by said target domain from said hybrid of said first domain with said second domain is energetically more favored than ii. the free energy of displacement of said second domain by said off-target domain from said hybrid of said first domain with said second domain.

In the molecular construct of the present invention, the off-target domain may also be generally homologous with respect to the target domain. Further, in the molecular construct of the present invention, the off-target domain may also differ from the target domain either chemically by at least one functional group or conformationally or both. In a particular embodiment, the first and second domains may be on the same molecule or different molecules.

Further, in accordance with the present invention, a population of such molecular constructs may be provided. Such a population may comprise a. a first subpopulation of at least one said molecular construct with respect to a first target domain and b. a second subpopulation of at least one said molecular construct with respect to a second target domain, wherein said first target domain differs from said second target domain.

In a particular embodiment, the population comprises a. a first subpopulation comprising at least one said molecular construct with respect to a first off-target domain and b. a second subpopulation comprising at least one said molecular construct with respect to a second off-target domain, wherein said first off-target domain differs from said second off-target domain.

As explained hereinabove, molecular constructs and populations thereof may be in solution (spatially unconstrained) or may be spatially constrained, such as in competitive surface probes (hereinafter "CSPs"; e.g., competitor-probe complexes linked to a solid support) as are more fully described hereinafter. Spatially constrained populations and subpopulations thereof are may be presented in accordance with the present invention as arrays.

It should be noted that the term "differentiating" may include detection, identification, quantification, surveillance, diagnosis, genotyping, profiling, fingerprinting, isolating, and/or a combination thereof of a target molecule from an off-target molecule, and even separation and/or purification.

In accordance with the instant invention, arrays for differentiating, such as detecting and quantitating, target molecules are provided. In a particular embodiment, the array comprises more than one biosensor element on a solid support, wherein each biosensor element comprises a specific binding pair (e.g., comprising a probe and a competitor) linked to the solid support. Each member of the specific binding pair may individually be a nucleic acid, peptide nucleic acid, or other hybridizable entity. The arrays of the instant invention may comprise more than one series (subset) of biosensor elements (e.g., about 2 to about 100 (or more), about 2 to about 20, about 2 to about 10, or about 5 to about 10 biosensor elements). Each series of biosensor elements may be designed towards a specific or different target molecule. In a particular embodiment, each biosensor element of a series comprises the same probe (and/or competitor) in the specific binding pair of each biosensor element of the series. In still another embodiment, each series of biosensor elements comprise a different competitor (or probe) in the specific binding pair of each biosensor element of the series, wherein the different competitors have different binding affinities for the probe (e.g., by having different or more mismatches).

In accordance with the instant invention, kits comprising at least one array of the instant invention are also provided. The kits may further contain buffers.

According to another aspect of the instant invention, methods of detecting the presence of a target molecule and/or quantitating the amount of a target molecule in a sample are also provided. The methods comprise contacting the sample with the competitor-probe complexes (e.g., an array) of the instant invention and detecting/monitoring the presence of the target molecule or molecules. The method may comprise washing unbound molecules from the array, but does not require wash steps. The method may also comprise a denaturing step such as a heating step to disrupt the specific binding pairs on the array, optionally, while cooling in the presence of the target molecule sample. The method may also comprise a step involving solution or solvent changes in order to disrupt specific binding pairs (e.g., changes in temperature (e.g., heating), changing the pH and/or adding a denaturant (e.g., urea, guanidine hydrochloride, and the like). In particular embodiments, the target molecule is detectably labeled (e.g., with an isotope, radioisotope, fluorescent compound, etc.). In other embodiments the target molecule is not labeled. In yet another embodiment, the target molecule for the surface probes may be part of a solution probe for binding a solution target. In this manner a labeled solution probe molecule can be released from complex with an unlabeled target in solution and thereby provide a labeled molecular entity for binding to the surface probes.

False positives in research and diagnostics represent a significant limitation of increasingly sensitive biosensor technologies. Attempts to overcome false positives by reducing sensitivity will lead to an increase the likelihood of false negatives. The technology of the present invention provides an approach to overcome this trade-off between false-positives and false-negatives. Molecular components of the present invention are exemplified and provided by Competitive Surface Probes (CSPs). The integration of CSPs into Quantitative Recognition Arrays (e.g. DNA-meters and Apta-meters) provides means to a) quantify target concentrations and b) substantially reduce the occurrence of false-positives in research and diagnostic assays. By carefully matching the competing thermodynamics of self-hybridization and target binding, CSPs allow target binding specificity to be maintained, while binding affinity is attenuated over a range useful for biotechnological and diagnostic applications. For the DNA-meter, the targets are specific nucleic acid molecules. For the Apta-meter the targets are proteins, small-molecules, or other molecular entities for which nucleic acid aptamers have been discovered. In either case, the Quantitative Recognition Array provides a series of digital switches that define the target identity and concentration by the types and numbers of switches of each type that are turned "on". The experimental results described herein may utilize fluorescence detection technologies as output signaling means. However, the fundamental features of CSPs and Quantitative Recognition Arrays are independent of platform, and are thus applicable to a wide variety of biosensor technologies.

The conceptual basis of the competitive surface probes (CSP) technology of the present invention derives in part from solution competitive probes (Gelfand et al. (1999) Proc. Natl. Acad. Sci., 96:6113-8; Plum et al. (2001) Biopolymers 61:214-23), from the nucleic acid switches for protein sensing and screening (DeCiantis et al. (2007) Biochem., 46:9164-73), from tunable affinity ligand and bimolecular probes concepts, and from studies of DNA triplex stability (Roberts et al. (1991) Proc. Natl. Acad. Sci., 88:9397-401). The integration of CSPs into quantitative biorecognition arrays represents a cross-platform molecular technology of the present invention empowering the development of biosensors.

A Quantitative Recognition Array of the present invention may comprise a series of molecular construct biosensor elements, with each element coated with one of a series of Competitive Surface Probes (CSPs). Each CSP will turn "on" if its target concentration exceeds a certain threshold. Target identities and concentrations are thus defined by the unique sequence of CSPs that are turned "on". As described below, even though individual CSPs may show cross-reactivity under some target concentrations, the pattern of CSP switching can be used to uniquely define target identities and concentrations over a wide range of total target concentration. Hence, the incorporation of arrayed CSPs (e.g., DNA-meters or Apta-meters) onto biosensor surfaces provides a powerful and widely applicable solution to the problems of false-positives and of low-cost quantification for a wide range of research and diagnostic applications.

Figure 1B:
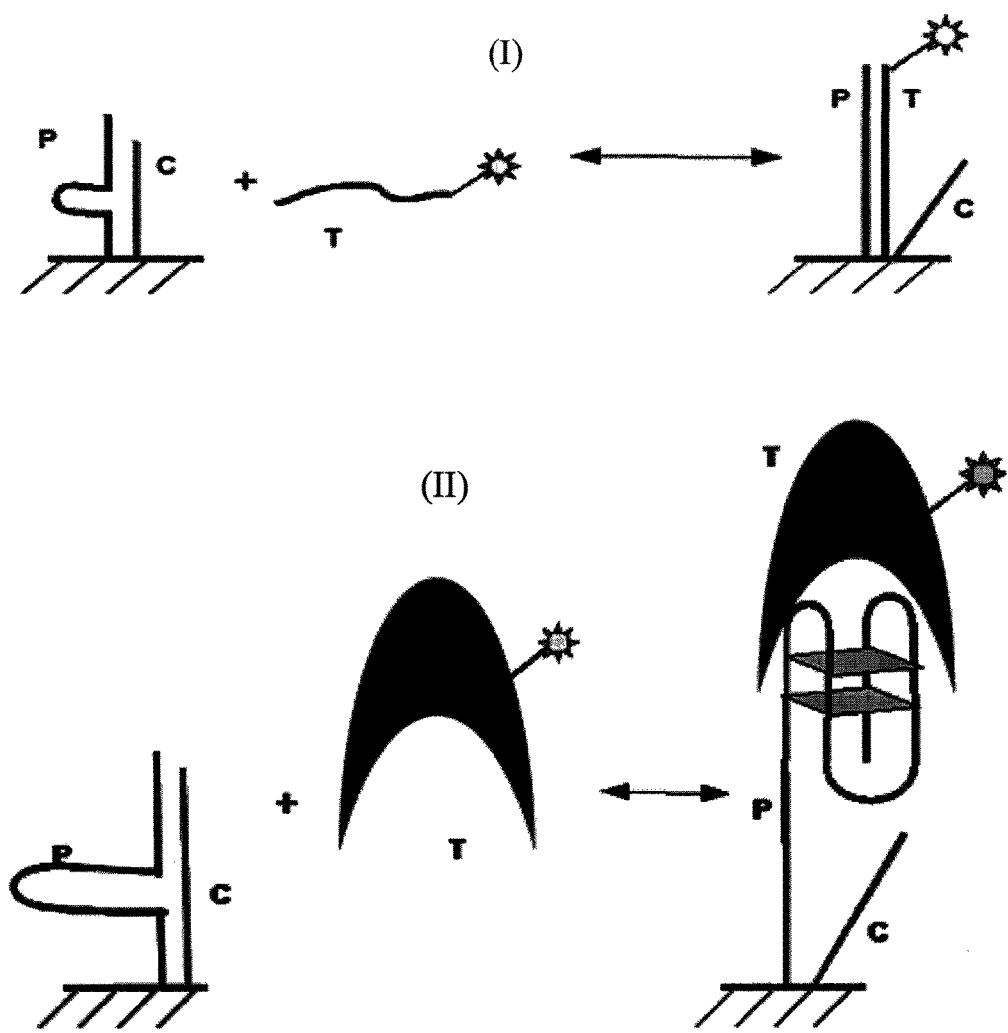
FIG. 1B provides a schematic of the action of competitive surface probes. Strands P (probe) and C (competitor) are attached via neighboring groups on the surface. C is partially complementary to P. The target T binds P and displaces C. (I) T is a nucleic acid strand complementary to P. (II) T is a protein target to the aptamer P. In a particular embodiment of the instant invention, the P and C labeling may be reversed in the probe complex.
Figure 1C:
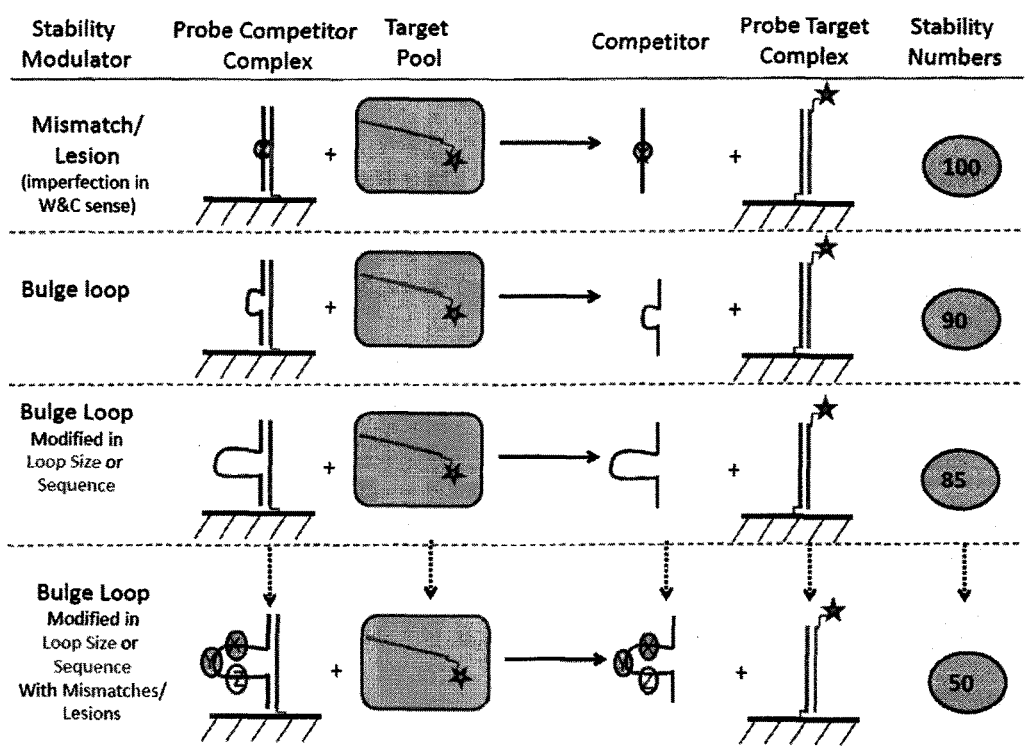
FIG. 1C also provides a schematic of an embodiment of the instant invention.
Figure 2A:
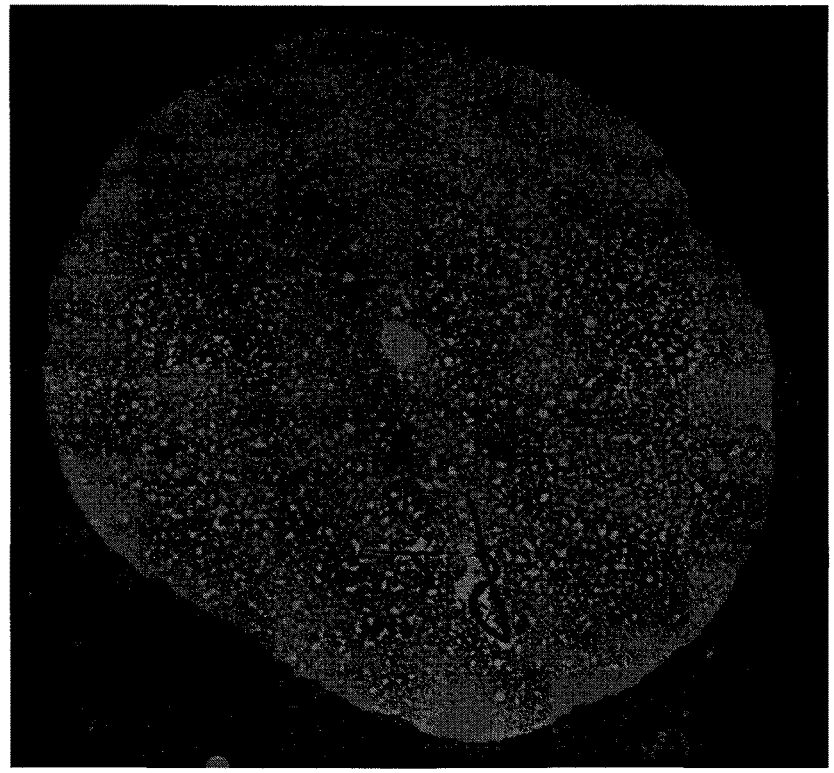
FIGS. 2A-2D provide images of results obtained from the interactions of competitive surface probes with Cy3 labeled targets. Target concentrations are as illustrated under each figure.
Figure 2B:
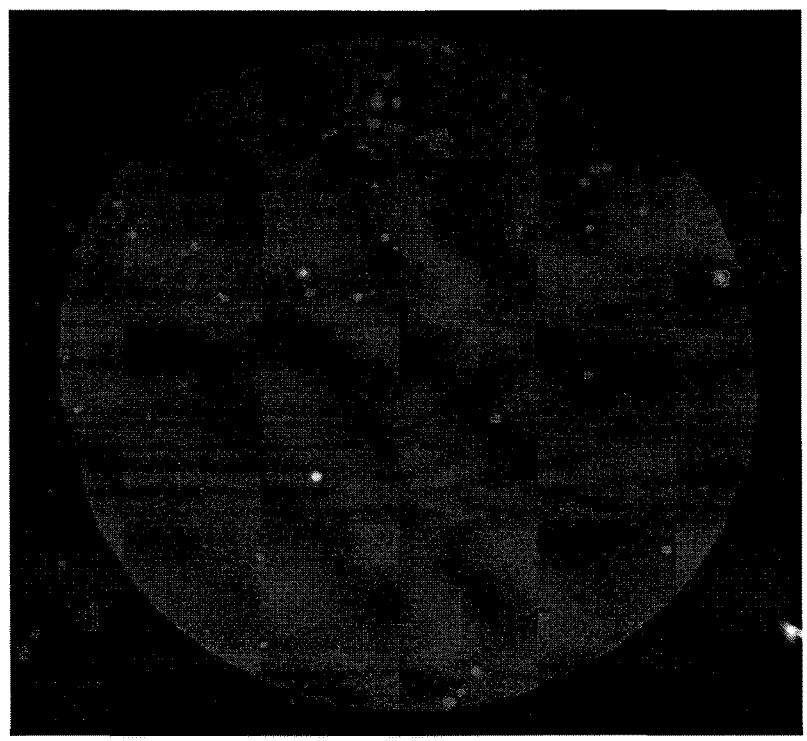
Figure 2C:
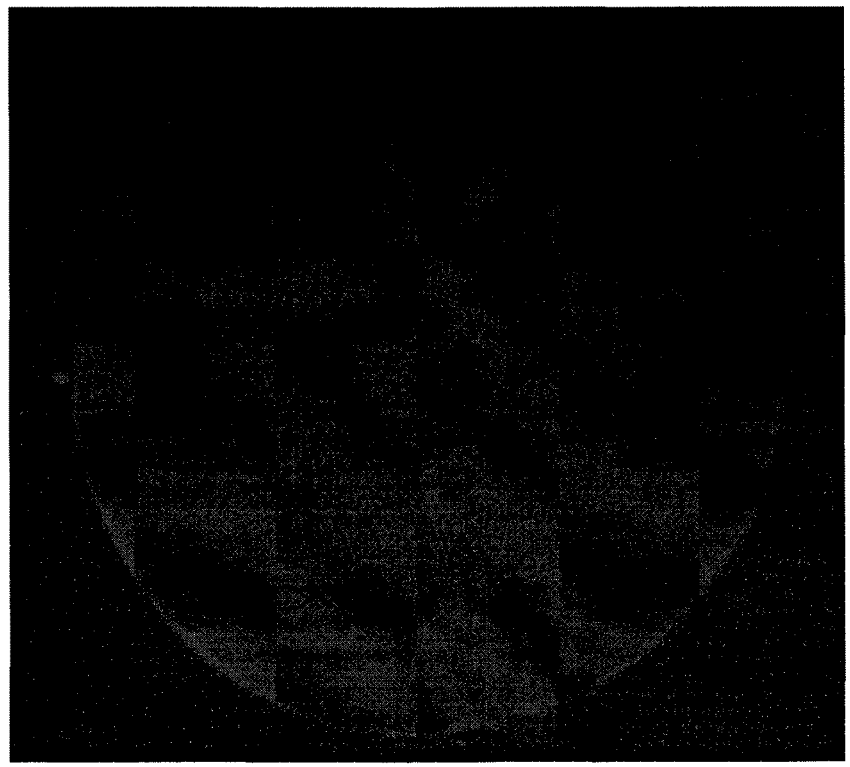
Figure 2D:
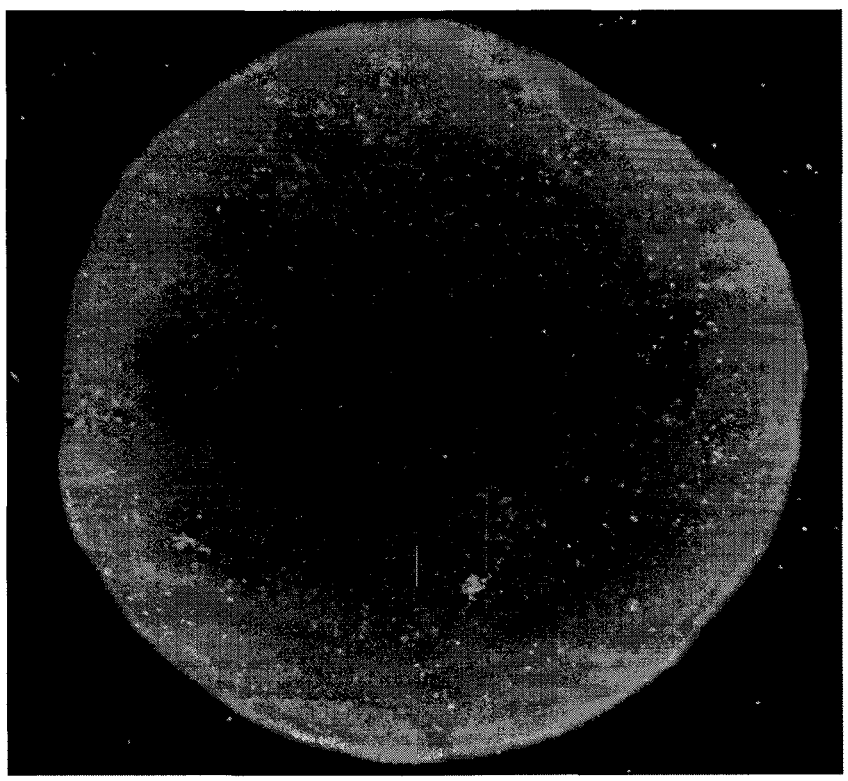

If the CSP-coated elements for a single nucleic acid target are arranged left to right from lower to higher threshold, then a model DNA Meter will manifest the behavior shown in FIG. 1A. If the CSP-coated elements are based on aptamers for a single target, then FIG. 1A can equally well represent a model Apta-meter. Key features of CSPs are illustrated in FIG. 1B. These constructs comprise two strands that are attached to a surface within a hybridizable distance of each other. The probe strand P binds the target and the competitor strand C is designed to hybridize with a range of affinities to P. Depending on the context, the C strand may have environmentally sensitive switch elements.

In its most basic form, under a defined set of solution conditions, both the DNA-meter and the Apta-meter provide a digital readout of target identity and concentration based on which of a series of engineered probes are turned on and which remain off. Since hundreds of individual biosensors can be arrayed on a surface, such as a coverslip, multiple digital readouts can be obtained for multiple targets, allowing for the precise determination of scores of individual target concentrations. For the DNA-meter, when combined with initial rapid pre-amplification steps, e.g. by end-point PCR or isothermal amplification methods, the technology of the present invention represents a highly attractive and cost-effective alternative to qPCR for diagnostic applications. For the DNA-meter, by utilizing multiple probes per target and multiple targets per amplicon, the presence of genetic anomalies is readily detected by a decrease in the number of probes turned on for the mutated target compared to other targets on the same amplicon. Similarly, for the Apta-meter, closely related target proteins can be discriminated, e.g., proteins that differ by the extent or nature of post-translational modification.

In contrast to traditional microarray measurements, for which slides are dried prior to imaging, for Quantitative Recognition Arrays, measurements may be made for arrays that are immersed in target solution.

CSPs modified with 5' and 3' amino groups may be attached as functional bimolecular probes to dextran coated slides (see, e.g., PCT/US2006/047523). Because CSPs are bound to dextran polymers, their behavior is significantly more "solution-like" than for typical arrays that are coated in a two-dimensional manner on the top of a glass slide. Dextran polymers may be replaced by other spacer groups such as oligo-T regions and PEG spacers. The instant approach allows for the focus on specific interactions rather than on artifacts relating to surface effects.

Briefly, dextran may be covalently coupled to epoxy-silanated slides and subsequently activated with $NaIO_4$ to create pairs of reactive aldehydes by partial oxidation of some of the carbohydrate monomers at cis-hydroxyl positions. Typically, gels are dried to ~50% humidity prior to spotting. In other embodiments, arrays of CSPs may be prepared on the slides as follows: First, C6 amino CSPs may be dissolved in 50 mM $NaHCO_3$ pH 8.5 with 100 mM KCl and 4 mM $MgCl_2$ to a concentration of between 1-10 µM. Just before spotting, $NaCNBH_3$ is added to a concentration of 100 mM. The dried gel is spotted and allowed to sit at room temperature in 50% humidity overnight. Then, the slide is treated with 50 ml of 1 mg/ml NaBH4 for 30 minutes at room temperature to deactivate any remaining aldehdye groups, washed with several changes of water, 20% propanol, and finally hybridization buffer before incubation with the target.

CSPs provide many advantages. For example, similar targets can be distinguished over a wide range of concentrations with CPSs. For solution probes, the concentration of probe-target complex must be in the nanomolar range or higher in order for a significant fluorescence signal to be monitored. However, if the probe-target complex concentration is in the nanomolar range, then the total concentrations of both probe and target must be at least in this range as well. If the equilibrium dissociation constant for the formation of probe-target complex is sub-nanomolar, then the binding of target to probe will be essentially quantitative, and binding curves, as monitored by fluorescence, will not depend significantly on the details of the probe utilized. Moreover, small differences between targets, will be impossible to discern based on equilibrium curves alone. In stark contrast, for CSPs the concentration of target will typically be in significant excess over that of surface-bound probe, and the fraction of probe bound will be defined by a) the equilibrium constant for probe-target association and b) the concentration of free target in solution. Hence, in this case, the observed signal will depend significantly on both the nature of the probe and target molecules and on the free concentration of target.

Figure 3:
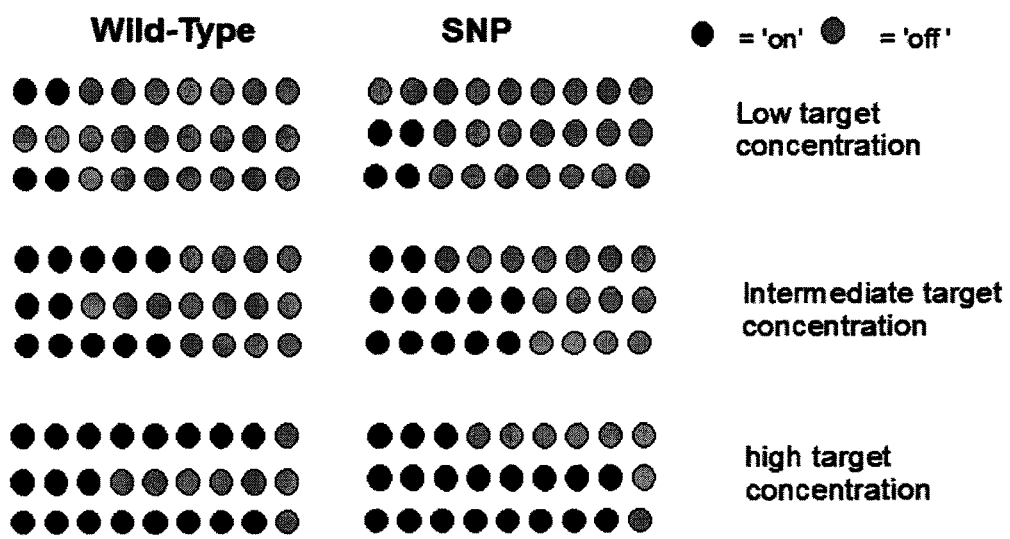
FIG. 3 provides an illustration of how the DNA meter can be used to distinguish between single nucleotide polymorphisms (SNPs). For the wild-type, a characteristic pattern of competitive surface probes (CSPs) turned "on" is observed. When a SNP occurs, the pattern of probes turned "on" helps to define which SNP is prevalent.

In addition to the above, CSPs provide a high level of multiplexing capacity. Individual sensor elements can be derivatized with different surface probes in order to obtain a signature of the type and nature of targets in solution. Discrimination is based on the position of individual probes within the surface array and does not require the simultaneous monitoring of multiple fluorophores. One useful aspect of this multiplexing capability is as follows: consider a DNA meter with multiple competitive surface probes for each target on a particular amplicon and with multiple targets per amplicon. The DNA meter will respond in a characteristic pattern of "on" signals to increasing amplicon concentration. However, this pattern will be perturbed if one of the target sequences on the amplicon has a SNP. In this case, all of the probes for that particular target will turn on at higher concentrations than anticipated, compared to the probes for the other targets on that amplicon. Consequently, the multiplexing capability of the DNA meter will allow the accurate and sensitive detection of SNPs. The principle behind this application of CSPs to determine SNPs and other genetic abnormalities is shown in FIG. 3.

Similarly, for the Apta-meter, closely related proteins and small molecules can be distinguished by utilizing arrays of aptamers that target different regions of target proteins or small molecules. Hence, the Apta meter technology of the present invention is facilitated by aptamer discovery methods such as those utilized by Orthosystems, Inc. which typically return a number of different aptamers for the same target, with different affinities and recognition regions. The consequences of this enhanced stringency of the Apta-meter for diagnostic applications is a significant elimination of false positive in diagnostic applications, e.g. for cardiac or cancer biomarkers. The ability to reduce false-positives for low-cost point-of-care devices under situations where rapid therapeutic decisions must be made in turn represents a diagnostic tool with wide-ranging public health implications.

CSPs are designed using principles of oligonucleotide thermodynamics to create a series of metastable probe-competitor pairs that differ in stability in the presence of target. A series of CSPs for detecting and quantitating a specific target domain will typically all contain the same probe (assuring identical hybridization specificity for each individual CSP) but different associated competitors which serve to modulate hybridization affinity through competitive equilibrium with the target domain. This results in the differing concentration dependent response of the target to each individual CSP even though they all have the same specificity in target binding.

The DNA meter comprises a series of digital switches that define nucleic acid target identities and absolute concentrations by the types and numbers of switches of each type that are turned "on". When applied to the analysis of PCR amplified products, the DNA meter will provide rapid identification and quantification of DNA targets after a limited number of cycles. Besides being more rapid than conventional qPCR, the DNA meter can be used to rapidly localize mutations that would not be apparent with conventional qPCR. For situations where a fixed series of target molecules must be repetitively determined, and/or screened for mutations, the DNA meter thus provides a rapid, cost-effective and significantly more informative alternative to qPCR. In addition to providing an alternative to qPCR, DNA meters can enhance qPCR by being directly integrated as detection arrays into qPCR machines. In this embodiment, the technology of the present invention provides a powerful tool for quantitative mutational and gene expression analysis.

In one embodiment, the "target" for the competitive surface probe could also be a fluorescently labeled solution probe that binds the analyte (biologically relevant target) in solution. When the analyte is absent, then the solution probe binds as a "target" to the competitive surface probe, and the spot lights up indicating the absence of analyte. In the presence of analyte, the spots would then turn off, in a concentration dependent manner. An alternative means of doing the same thing would be to have the "target" for the surface binary probe to be labeled with quencher, and have the binary probe labeled with fluorophore. In this case the presence of analyte would remove the surface-bound quencher, causing the spots to light up in a concentration dependent manner. This embodiment represents a solution binding but surface monitoring version of a self-reporting quantitative recognition array.

The invention described herein builds on the use of solution competitive probes for rapid thermodynamic screening. However, in contrast to the prior solution work, which is limited by the concentrations required for spectroscopic or thermodynamic measurements, molecular constructs of the present invention, such as surface probes, allow measurements to be accessible over a very wide range of target concentrations. When configured such that the targets for the CSP probes are themselves probes for solution analytes, then the quantitative surface arrays provide a label-free means of monitoring interactions in solution. DNA meters comprising arrays of CSPs targeting multiple regions per amplicon may be integrated into a variety of biosensor detection schemes in order to facilitate the rapid identification and localization of genetic anomalies. Apta-Meter arrays also allow precise, multicomponent analysis of complex biological samples. Consequently, DNA meter and Apta-Meter technology of the present invention may be used in a range of research, forensic and diagnostic applications.

Other examples for using the quantitative recognition arrays of the instant invention include surveillance, diagnosis and genotyping of antibiotic-resistant bacterial infections (e.g., *S. aureus, C. difficile*), and neonatal genotyping. The technology of the present invention is also uniquely suited for forensic applications. A model DNA-meter may be designed for its ability to define short tandem repeat (STR) length distributions on-chip, by a hybridization-based assay not involving electrophoretic separation. Applications relevant to the therapeutics include, without limitation, on-line sensors for bioprocess quality control of antibodies and other therapeutic proteins. The technology of the present invention may also be used for rapid monitoring of air, water and food for potential toxic and/or infectious agents.

Definitions

"Molecular construct" means a molecular structure, complex, or a part thereof and includes, for example, a probe complex. A "probe complex" may be a molecular construct comprising a target-binding domain.

"Energy landscape" means the points of an energy surface mapping possible conformations of a molecular structure with their corresponding Gibbs free energy levels on a two-, or three-, or n-dimensional coordinate system. The coordinate system would include averaged intermolecular spatial coordinates (e.g. x, y, and z) as well as coordinates relating to thermodynamic ensemble variables (e.g. temperature, pressure, concentration).

"Feature density" means the number of molecular constructs per spatial unit, that is per unit length for a one spatial dimension system, per unit area for a two spatial dimension system, per unit volume for a three spatial dimension system.

"Metastable equilibrium" means a local Gibbs free energy minimum of a state on an energy landscape comprising the initial Gibbs free energy ground state of an unhybridized probe and an unbound target (or an unhybridized probe and an unbound off-target, as the case may be) and the final Gibbs free energy ground state of a probe-target complex (or a probe-off-target complex, as the case may be), the initial ground state being at a higher Gibbs free energy than the final ground state.

As used herein, the term "stable" may refer to a free energy state that is preferred over alternative free energy states under a defined set of conditions, including, e.g., temperative, ionic conditions and the presence or absence of substances, molecules or environmental factors that influence molecular or intermolecular conformation. Stability does not imply indefinite irreversibility, but may be used in reference to various states of relative irreversibility, quasi-irreversibility, pseudo-irreversibility, quasi-reversibility or pseudo-reversibility as used in the art. Quasi-irreversible states include, for example, "metastable states" as defined herein.

The phrase "solid support" refers to any solid surface including, without limitation, any chip (for example, silica-based, glass, or gold chip), glass slide, membrane, plate, bead, solid particle (for example, agarose, sepharose, polystyrene or magnetic bead), column (or column material), test tube, or microtiter dish/plate. Solid support may be made out of, without limitation, nitrocellulose, glass, polystyrene, polypropylene, polyethylene, dextran, nylon, amylases, natural and modified celluloses, polyacrylamides, gabbros, and magnetite.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

The term "DNA-meter" as used herein contemplates not only meters based on DNA and alternatives stated herein, but is also intended to refer to meters based on DNA analogs, RNA, RNA analogs and, more generally, nucleic acids and nucleotide-based molecular mimics, where molecular mimics are natural or synthetic nucleotide molecules or groups of molecules designed, selected, manufactured, modified or engineered to have a structure or function equivalent or similar to the structure or function of a different nucleotide molecule or group of molecules. Examples of such DNA and RNA analogs include but are not limited to backbone modifications (e.g. locked nucleic acids, peptide nucleic acids), base modifications, xeno-nucleic acids (Pinheiro et al. (Science (2012) 336:341-344), abasic sites and unnatural base analogs.

The term "Apta-meter" as used herein contemplates not only to meters based on nucleic acid aptamers and alternatives stated herein, but is also intended to refer to meters based on nucleic acid analogs, including backbone modifications (e.g. locked nucleic acids, protein nucleic acids) base modifications, abasic sites, unnatural base analogs and synthetic non-nucleic acid molecules with structural and recognition features designed to mimic known aptamers. Aptamers include single-stranded, partially single-stranded, partially double-stranded or double-stranded nucleotide sequences capable of specifically recognizing a selected nonoligonucleotide molecule or group of molecules by a mechanism other than Watson-Crick base pairing or triplex formation. Aptamers disclosed herein include, without limitation sequences comprising nucleotides, ribonucleotides, deoxyribonucleotides, nucleotide analogs, modified nucleotides and nucleotides comprising backbone modifications, branchpoints and nonnucleotide residues, groups or bridges. They may be partially and fully single-stranded and double-stranded nucleotide molecules and sequences, synthetic RNA, DNA and chimeric nucleotides, hybrids, duplexes, heteroduplexes and any complex, conjugate or nucleotide-base molecular mimic thereof.

As used herein, a "biological sample" refers to a sample of biological material obtained from a subject, particularly a human subject, including a tissue, a tissue sample, a cell sample, a tumor sample, and a biological fluid (e.g., blood or urine).

The term "probe" as used herein refers to an oligonucleotide, polynucleotide, nucleic acid, either RNA or DNA, or other hybridizable entity (e.g. PNAs, locked nucleic acids, or other base or backbone modifications), whether occurring naturally as in a purified restriction enzyme digest or produced synthetically, which is either a) capable of annealing with or specifically hybridizing to a nucleic acid with sequences complementary to the probe or b) capable of binding with high affinity to a non-nucleic acid target. A probe may be single-stranded, double-stranded, or multistranded. The exact length of the probe will depend upon many factors, including temperature, source of probe and use of the method. For example, for diagnostic applications, depending on the complexity of the target sequence, the oligonucleotide probe typically contains about 10-100, about 10-50, about 15-30, about 15-25, about 20-50, or more nucleotides, although it may contain fewer nucleotides. The probes herein may be selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target, although they may. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

The term "oligonucleotide" as used herein refers to nucleic acids, sequences, primers and probes of the present invention, and is defined as a nucleic acid molecule comprised of two or more ribo- or deoxyribonucleotides (or analogs thereof), preferably more than three. The exact size of the oligonucleotide will depend on various factors and on the particular application and use of the oligonucleotide.

"Nucleic acid" or a "nucleic acid molecule" as used herein refers to any DNA or RNA molecule, single, double, or multi stranded and, if single stranded, the molecule of its complementary sequence in either linear or circular form. Nucleic acid molecules of the instant invention may be oligonucleotides or synthetic polynucletides and selected nucleic acid sequences which may optionally be conjugated to one or more nonoligonucleotide molecules. Nucleic acid molecules of the instant invention may comprise one or more modifications such as backbone and/or base modifications/analogs (e.g., LNAs) or xeno-nucleic acids. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

The term "nucleotide" includes nucleotides and nucleotide analogs, preferably groups of nucleotides comprising oligonucleotides, e.g., any compound containing a heterocyclic compound bound to a phosphorylated sugar by an N-glycosyl link or any monomer capable of complementary base pairing or any polymer capable of hybridizing to an oligonucleotide.

The term "nucleotide analog" refers to molecules that can be used in place of naturally occurring bases in nucleic acid synthesis and processing, preferably enzymatic as well as chemical synthesis and processing, particularly modified nucleotides capable of base pairing and optionally synthetic bases that do not comprise adenine, guanine, cytosine, thymidine, uracil or minor bases. This term includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-ß-cyanoethyl phosphoramidites, methylenephosphonates, phosphorodithioates, peptide nucleic acids, achiral and neutral internucleotidic linkages and nonnucleotide bridges such as polyethylene glycol, aromatic polyamides and lipids.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g., chromatographic methods, agarose or polyacrylamide gel electrophoresis, HPLC analysis, and the like).

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

As used herein, the term "array" refers to an ordered arrangement of hybridizable array elements (e.g., polypeptides, proteins, nucleic acids, antibodies, small molecules, etc.). The array elements are arranged so that there are at least one or more different array elements on a solid support. The array elements may be arranged in one or more dimensions. In a particular embodiment, the array elements comprise oligonucleotide probes.

As used herein, a "specific binding pair" comprises a specific binding member and a binding partner which have a particular specificity for each other and which in normal conditions bind to each other in preference to other molecules. Examples of specific binding pairs include, without limitation, antigen-antibody, receptor-hormone, receptor-ligand, agonist-antagonist, lectin-carbohydrate, nucleic acid (e.g., RNA or DNA) hybridizing sequences, nucleic acid-protein, and polypeptide-small molecule. Various other specific binding pairs are contemplated for use in practicing the methods of this invention, such as will be apparent to those skilled in the art.

The following non-limiting examples are provided to further illustrate the present invention.

Example 1

A DNA-meter was constructed which can distinguish *S. aureus* VanA target from MecA target. The DNA-meter also shows a concentration-dependent response over a wide concentration range. Specifically, a set of five CSPs was designed (Table I). Table 1 provides the $T_{1/2}$ concentrations at 30° C. These CSPs were used to derivatize dextran-coated slides with spots. The slide yielded a concentration-dependent capture of target and was able to discriminate between target mecA from off-target vanA. It was also demonstrated that vanA target lights up spots derivatized with a surface bound vanA probe, but not spots derivatized with any of the mecA probes. The lower limit of target monitored was 100 fM and the upper limit was 100 nM. The results of these experiments are summarized in Table II.

TABLE I

CSPs used to derivatize dextran.

| Probe name | Probe Strand (SEQ ID NO) | Competitor Strand (SEQ ID NO) | $(T_{1/2})_{calc}$ |
|---|---|---|---|
| MecPQT1 | TATGTATGCT TTGGTCTTTC TG-NH$_2$ (1) | none | 5 × 10$^{-18}$ M |

TABLE I-continued

CSPs used to derivatize dextran.

| Probe name | Probe Strand (SEQ ID NO) | Competitor Strand (SEQ ID NO) | $(T_{1/2})_{calc}$ |
|---|---|---|---|
| VanP0 | NH$_2$- GTGAGGTCGG TTGTGCGGTA TTGGG (2) | none | 1 × 10$^{-18}$ M |
| MecPQ3 | TATGTATGCT TTGGTCTTTC TG-NH$_2$ (1) | NH$_2$-CAGAAAGACT TTTTTTTGC ATACATA (3) | 138 fM |
| MecPQ8 | TATGTATGCT TTGGTCTTT CTG-NH$_2$ (1) | NH$_2$-CAGAAAGACC TTGCATACAT A (4) | 17 pM |
| MecPQ14 | TATGTATGCT TTGGTCTIT CTG-NH$_2$ (1) | NH$_2$-CAGAAAGACC AAAGCATACA TA (5) | 11 µM |

TABLE II

Probe Fluorescence for Various Target Concentrations.

| MecA target | VanA target | VanP0 | MecPQT1 | MecPQ3 | MecPQ8 | MecPQ14 |
|---|---|---|---|---|---|---|
| 100 fM | 0 | − | + | − | − | − |
| 1 pM | 0 | − | + | − | − | − |
| 10 pM | 0 | − | + | + | − | − |
| 100 pM | 0 | − | + | + | + | − |
| 10 nM | 0 | − | + | + | + | − |
| 100 nM | 0 | − | + | + | + | − |
| 0 | 100 nM | + | − | − | − | − |

In performing these initial experiments, polytetrafluoroethylene (PTFE)-coated glass slides with 4 mm diameter wells (SPI supplies, West Chester, Pa.) were used. The glass wells were uniformly coated with dextran, as described above. The use of PTFE-coated slides allowed for the use of the cover-slips to maintain a solution environment over the slides during the measurements and allowed for the complete immersion of the slides in target solutions. Into each well square arrays of 4 spots were manually spotted, using 0.3 µl of 10 µM solutions of amino-labeled probe. The volume of the pipeting was controlled by using a NanoFil™ syringe (World Precision Instruments, Sarasota, Fla.) that was modified to convert a defined turn of a screw to a defined linear distance of the syringe cylinder and, thus, to a reasonably well defined nanoliter volume of solution. Spots were pipetted onto the NaIO$_4$ activated dextran coated surfaces in the presence of NaCNBH$_3$. The resultant spots had diameters in the range of 200-400 µm and were well separated from each other. Subsequent reaction with NaBH$_4$ reduced any remaining aldehydes to hydroxyls. All spotting was performed at least in quadruplicate and each array of 4 spots had at least one control spot that was derivatized with a 10 mer directly labeled with Cy3. The presence of this spot provided us with the ability to accurately locate the other three spots, which corresponded to various combinations of the other probes listed in Tables I and II.

For the lower target concentrations tested, spotted slides were completely submerged in 50 ml centrifuge tubes containing target dissolved in 1×SSC buffer (150 mM NaCl, 15 mM sodium citrate, pH 7). In order to address potential hysteresis effects tubes containing microscope slides were heated to 90° C. and allowed to cool to room-temperature before removing slides, covering with target solution from the tube, and a cover-slip, and taking measurements.

In the presence of 100 fM through 1 pM of Cy3 labeled mecA target, the control spots and the spots derivatized with MecPQT1 probe lit up with fluorescence intensity in the Cy3 channel, but none of the other spots showed discernable signal. In the presence of 10 pM total concentration of mecA target the mecPQ3 probe spots also light up. For 100 pM mecA target, fluorescence is clearly observable for the mecPQ8 spots as well. For 100 fM through 100 nM mecA target, no fluorescence is apparent for either the vanA P0 probe spots or the mecPQ14 probe spots. When surface fluorescence for a target containing 1 µM labeled mecA probe was monitored, the background fluorescence of the solution prohibited monitoring surface fluorescence. Finally, in the presence of van A target at 100 nM total concentration, only the control spots and the vanA P0 probe spots show fluorescence when monitored using the Cy3 filter cube.

Representative spots are shown in FIG. 2. These spots were covered with MecA target solution at the concentrations indicated and imaged through a cover-slip. The exposure time for all images was constant at three seconds. Data were collected using a black and white camera and colorized using ImageJ software so that the most intense fluorescence was represented by white, followed by yellow, followed by green, followed by black.

Example 2

The basic features of the behavior of CxP probes, either in solution or attached to surfaces (CSPs), as for the DNA Meter and the Apta-Meter, reflect a very simple model:

$P_C \leftrightarrow P_H$ and $P_C+T \leftrightarrow P_T$, which are governed by the equilibrium expressions:

$K_1=(P_H)/(P_C)$ and $K_{lin}=(PT)/(P_C)(T)$, where $P_C$ and $P_H$ are, respectively, the coil and partially hybridized forms of the CxP probe (i.e., before target binding), and where PT is the probe-target complex. Making use of mass balance, these equations are easily solved to give $f_B$, the fraction of probe molecules that are bound by target. By setting $f_B=\frac{1}{2}$, an equation is obtained for the midpoint target concentration for ½ saturation of probe: $(T)_{1/2}=(1+K_1)/K_{lin}$. From this equation, it is apparent that as $K_1$ increases, the critical concentration shifts to higher total concentration. For solution measurements, a more relevant equation expresses the total concentration of target at half-saturation:

$(T_{tot})_{1/2}=(1+K_1)/K_{lin}+(P_{tot})$, where $(P_{tot})$ is the total concentration of probe in solution.

Figure 4A:
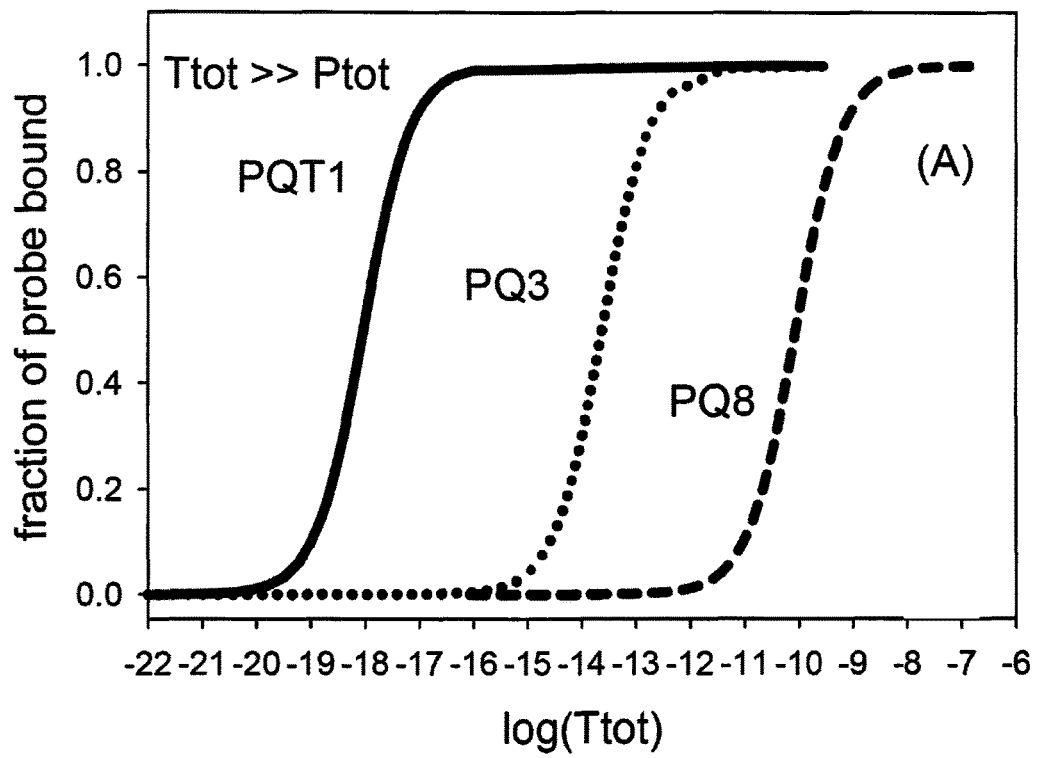
FIG. 4A shows 40° C. plots of the fraction of bound probe vs. total target concentration for target in excess compared to probe.
Figure 4B:
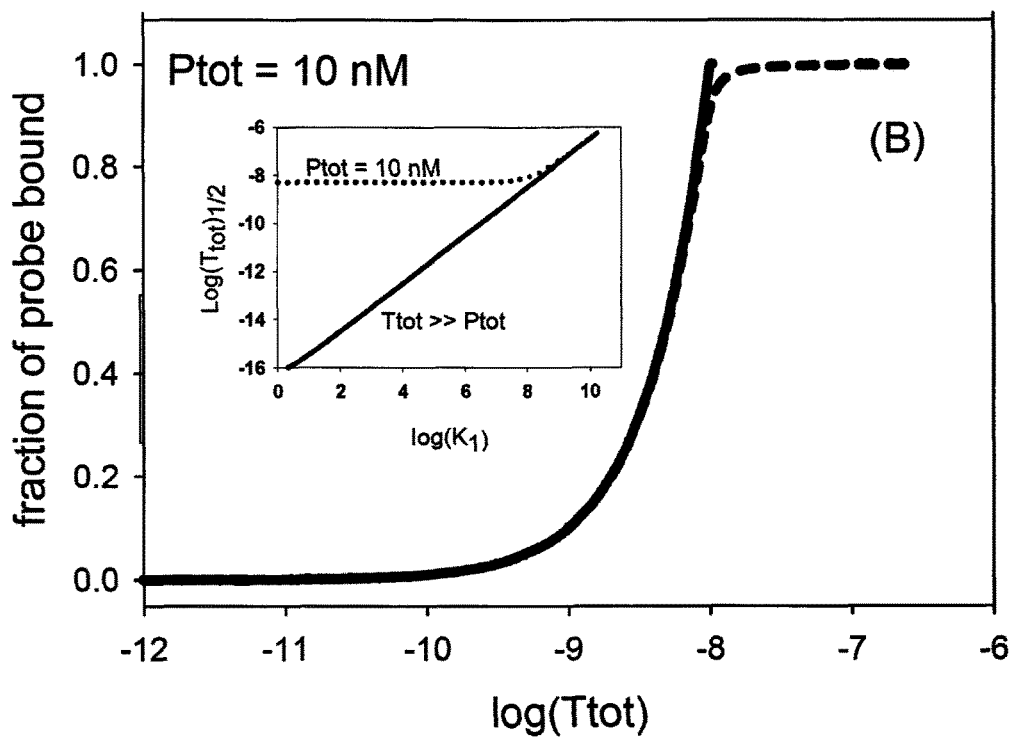
FIG. 4B provides 40° C. plots for probe concentration fixed at 10 nM. Inset is a plot of critical concentration for ½ saturation vs. $K_1$, with data on a log scale.
Figure 4C:
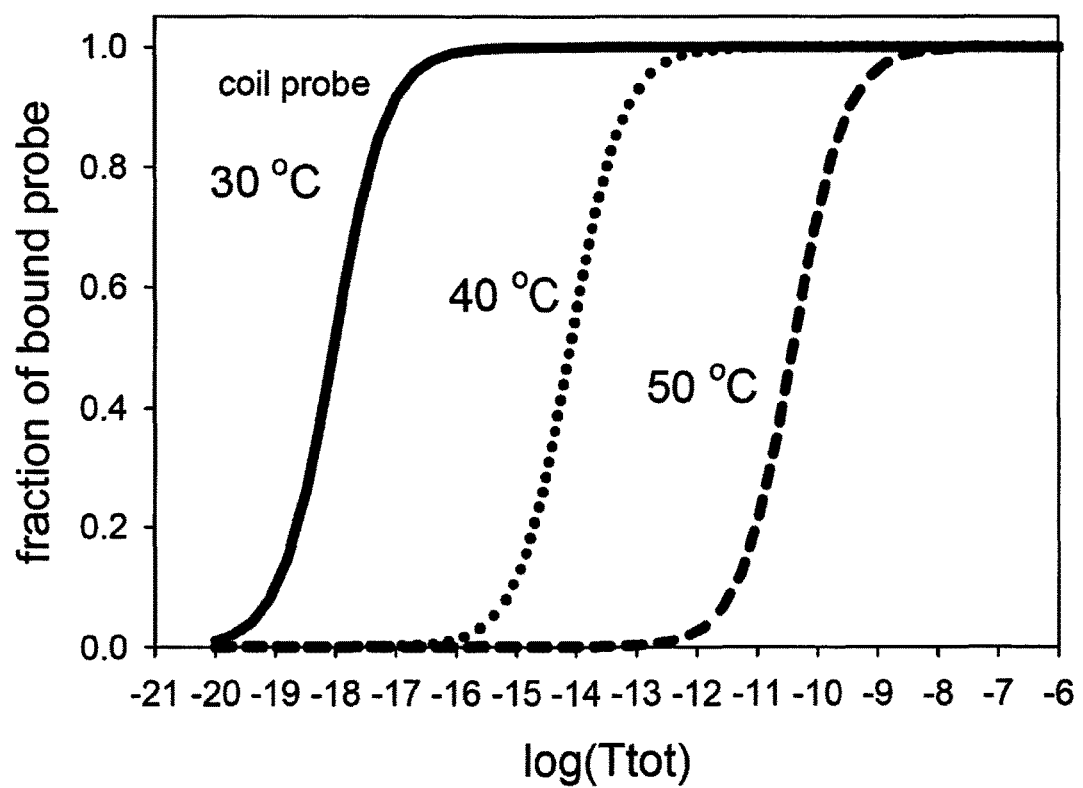
FIG. 4C shows curves at various temperatures for the coil probe, under conditions of excess target.

It is apparent that, in this case, half saturation does not typically occur until the target concentration approaches that of the probe. Simulations using this formalism are shown in FIG. 4. Two different situations are considered. For FIG. 4A, $(T_{tot})$ is taken to be in considerable excess compared to $(P_{tot})$, as would be the case for probes attached to biosensor surfaces. In FIG. 4B, $(P_{tot})$ is fixed at 10 nM, a typical value for solution fluorescence measurements. For comparison, FIG. 4C shows curves for the binding of the complementary coil probe to target as a function of temperature, again under conditions of excess target. Clearly, such temperature curves show significant similarity to the results of FIG. 4A, supporting the position that stringency can be enhanced by reducing affinity, in a similar manner using either temperature or competitive interactions.

In performing these simulations, competitive hybridization probes were designed based on a 30-base pair recognition sequence from the mecA gene (Sinsimer et al. (2005) J. Clin. Microbiol., 43:4585-91). This target sequence is given by TGCAGAAAGACCAAAGCATACATATTGAAA (SEQ ID NO: 6). The constant recognition sequence for this target is indicated by underlining. As probes, the sequence TT CAA TAT GTA TGC TTT GGT CTT TCT G (SEQ ID NO: 7) was used for strand P. Thermodynamic parameters for the formation of duplex from the target sequence binding to linear probe at 0.225 M NaCl are calculated using nearest neighbor methods (Markham et al. (2005) Nucl. Acids Res., 33:W577-81). The solution monomolecular constructs for which these simulations are made are shown in Table III, together with the calculated concentrations for half-saturation, $(T)_{1/2}$.

TABLE III

Ligands for simulations, with calculated $(T)_{1/2}$ at 30° C.

| Probe | Sequence (SEQ ID NO) | $(T)_{1/2}$ |
|---|---|---|
| PQT1 | TATGTATGCTTTGGTCTTTCTG (1) | 5 aM |
| Mec PQ3 | TATGTATGCTTTGGTCTTTCTG (1) CAGAAAGACTUTTTTTTGCATACAT A (3) | 138 fM |
| Mec PQ8 | TATGTATGCTTTGGTCTTTCTG (1) CAGAAAGACCTTGCATACATA (4) | 17 pM |

Even though these calculations are performed assuming that the target is a nucleic acid strand that hybridizes to the probe sequence, exactly the same formalism applies for binding of a protein to an aptamer sequence that is in equilibrium with a partially complementary competitive strand. For the aptamer case, the ability to fine-tune stringency via competitive interactions is particularly important since denaturation and aggregation can significantly limit the temperature range over which protein-ligand interactions can be interrogated.

Example 3

Experiments can be performed to monitor PCR in real-time chambers derivatized with CSP probes for S. aureus genes. The primers will be as described above for the S. aureus target genes (Sinsimer et al. (2005) J. Clin. Microbiol., 43:4585-91). S. aureus and other bacterial DNAs from normal and methicillin resistant strains will be obtained from ATCC. Bacterial DNA was sealed with buffer and enzymes in the chamber. PCR was performed using previously described protocols (Sinsimer et al. (2005) J. Clin. Microbiol., 43:4585-91). Chambers modified with CSPs were used to monitor the amplification of target sequences representing the SG16S, BAC16S, spa and mecA genes (Table IV). Following amplification, the amplified DNA was collected and subjected to gel-electrophoresis.

TABLE IV

Linear probes for S. aureus PCR.

| Gene | Linear probe sequence (SEQ ID NO) |
|---|---|
| BAC16S | 5'SH-$(CH_2)_6$-CGAGCTGACGACARCCATGCA3' (8) |
| SG16S | 5'SH-$(CH_2)_6$-CTTACCAAATCTTGACATCCT3' (9) |
| spa | 5'SH-$(CH_2)_6$-TTGTTGAGCTTCATCGTGT TG 3' (10) |
| mecA | 5'SH-$(CH_2)_6$-TTCAATATGTATGCTTTGG TCTTTCTG3' (7) |

Figure 5:
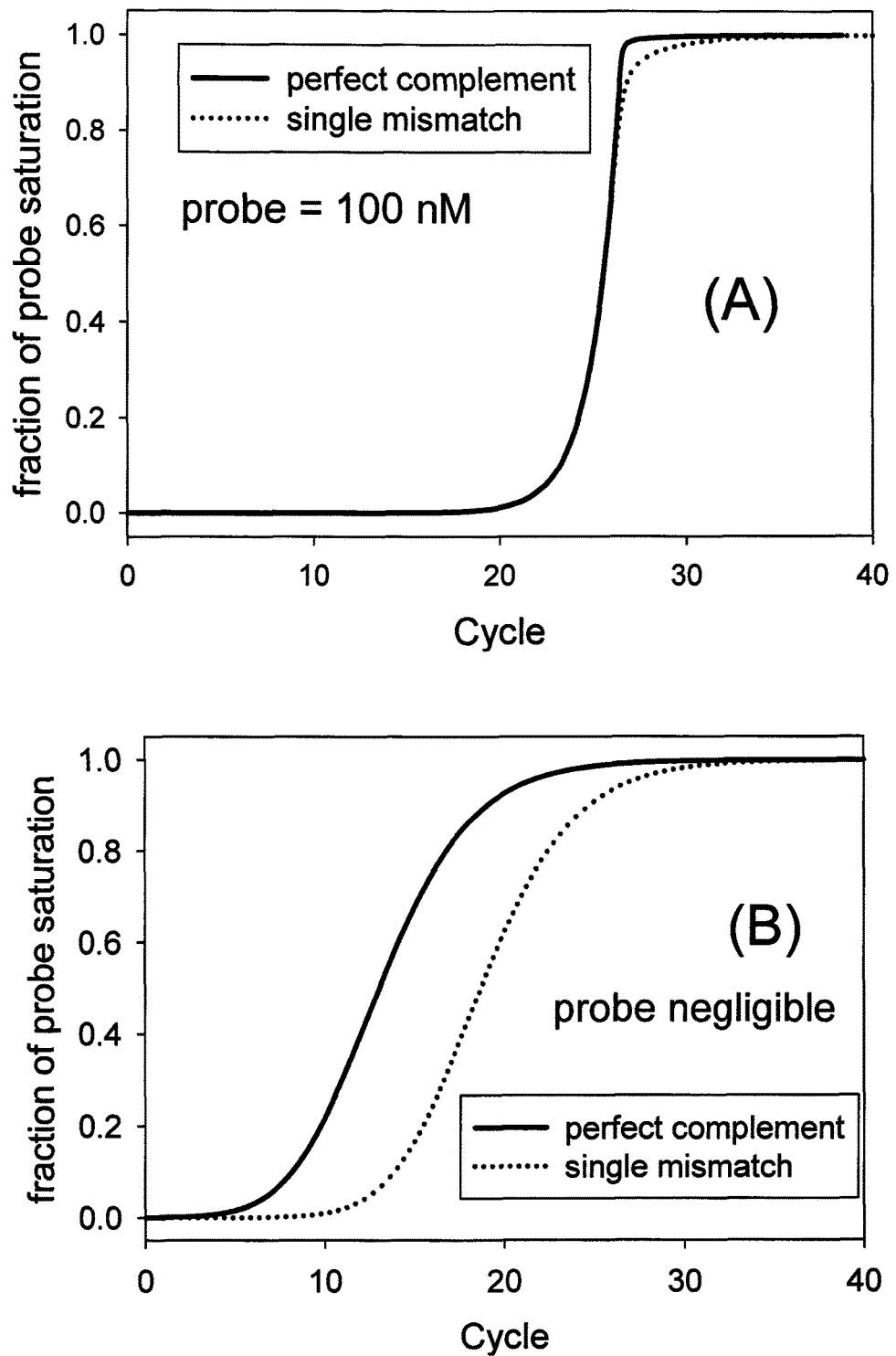
FIG. 5 provides simulations of PCR amplification of mecA target in the presence of mecA competitive surface probe. All calculations are for an annealing temperature of 50° C., and for a starting target concentration of $1 \times 10^{-15}$ M.

Preliminary results with the mecA gene have shown that having surface bound probes enhances sensitivity and thus reduces the number of cycles required to obtain a quantitative result. In comparison to using gel electrophoresis for analysis and quantification, the use of CSPs reduced by 75% the number of cycles required to obtain enough DNA for analysis. Moreover, using multiple probes for the same target sequences and multiple target sequences per amplicon both enhances quantitative accuracy and reduces the occurrence of false positives. Most significantly, the use of a DNA meter integrated into a quantitative PCR device will dramatically enhance the ability to discriminate SNPs, lesions and other genetic defects. In this application, series of CSPs can be designed to target multiple regions along individual amplicons. In the absence of mutations or other genetic anomalies, the order of turning on of CSPs for the particular sequences will show a characteristic pattern. In the presence of mutations, this order of turning on will deviate for those sequences where genetic anomalies occur. An illustration of this ability to distinguish genetic anomalies is shown in FIG. 5. In these calculations a competitive surface probe for the mecA gene from S. aureus was used and thermodynamic parameters were estimated from nearest neighbor calculations. The effect of competition for the target from the complement strand, which is assumed to be amplified at the same rate as the target strand, was included, thereby making the equations somewhat more complex than presented above. In FIG. 5A are calculations assuming a hypothetical solution molecular beacon probe with identical thermodynamic parameters as the CSP. For both simulations, an initial target concentration of $10^{-15}$ M and an efficiency of 1 is assumed. The molecular beacon concentration is taken as 100 nM, which is a value within the typical range used for molecular beacons in solution. From this curve a result is illustrated that is well-appreciated by practitioners of the molecular beacon art: It is impossible to distinguish closely related targets based on cycle number alone. In contrast, as is shown in FIG. 5B, when measurements can be performed for surface bound probes, where the concentration of target is in significant excess over the concentration of probe, then the cycle number is determined by the dissociation constant for formation of probe-target complex, and targets differing by as little as a single mismatch are readily distinguishable. As such, inexpensive electronic qPCR devices are developed for rapid, specific and highly sensitive detection of unlabeled nucleic acid targets.

Example 4

Figure 6:
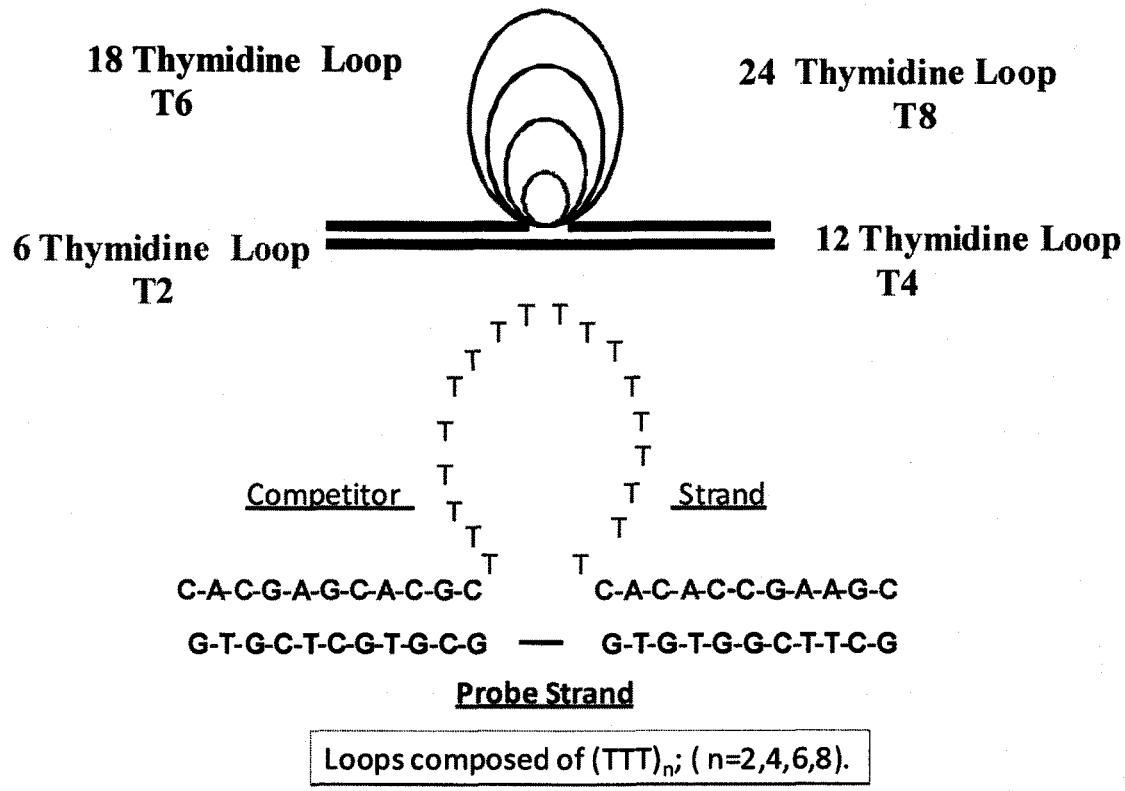
FIG. 6 provides a schematic of one manifestation of the Competitor•Probe (C*•P) complex for the DNAmeter in which the competitor probe complex is destabilized incrementally and in a predictable manner by increasing the size of a "recognition-neutral" T bulge loop in the centre of the competitor strand. Besides all-T bulge loops of varying size, numerous other modifications can be incorporated into the competitor strand to predictably modulate the stability of the "target recognition neutral" interaction between the competitor "masking tape" and the probe strand. The nucleotide sequences are SEQ ID NO: 11 (competitor strand) and SEQ ID NO: 12.

In one manifestation of the "tuning fork" probe concept described herein, the availability of the "free" probe strand (P) for binding/hybridizing to its complementary target domain (T) is systematically and predictably modulated. This modulation is achieved by pre-associating the probe strand with a family of competitor strands (C) of identical Watson Crick sequence recognition elements that are complementary to the probe, but which bind the probe with varying strengths due to incorporation into the C strand of "recognition-neutral" T bulge loops of increasing size, thereby creating a ladder of energetically tuned competitor strands (C*). The competitor-probe complex (C*P) becomes incrementally less stable with increasing bulge T-loop size, causing the competitor ("masking tape") strand (C*) to be more readily displaced at lower concentrations of target (T), thereby resulting in the formation of the final probe-target complex (PT); an event which corresponds to a successful "hit." FIG. 6 provides a schematic representation.

This design concept can be reduced to practice by either decorating a surface with or making a solution mixture of a family of energetically tuned C*P constructs ("tuning forks"), thereby forming an energetic ladder of probe complexes (C*P) against which one can titrate Target samples of increasing concentrations. In a successfully designed system, at the lowest target concentrations, "hits" (formation of the PT complex) will be detected initially by displacement of the least strongly bound "masking tape" C* strand. With increasing T concentrations, subsequent hits will sequentially be detected by and scale with the increasing stability of the C*P family of tuning fork complexes.

Figure 7:
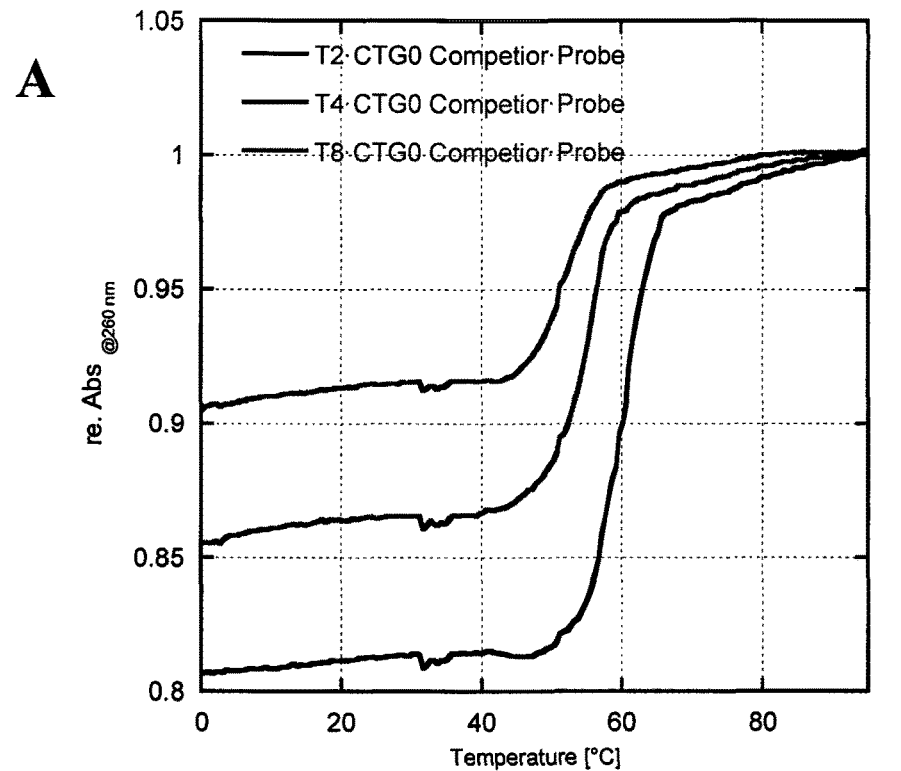
FIG. 7A provides normalized optical melting curves showing how a change in the "recognition neutral" T-bulge in the competitor strand modulates the thermal stability of the Probe•Competitor complexes (C*•P).
FIG. 7B provides normalized optical melting curves that result when equimolar amounts of Target (T) strand are added to the Probe•Competitor complexes (C*•P) in FIG. 7A. The strand displacement and exchange (C*•P and T to P•T and C) is seen in the UV melts wherein increasing the loop size in the competitor strand results in destabilized Probe•Competitor complexes and a lower temperature at which strand exchange occurs.
Figure 7:
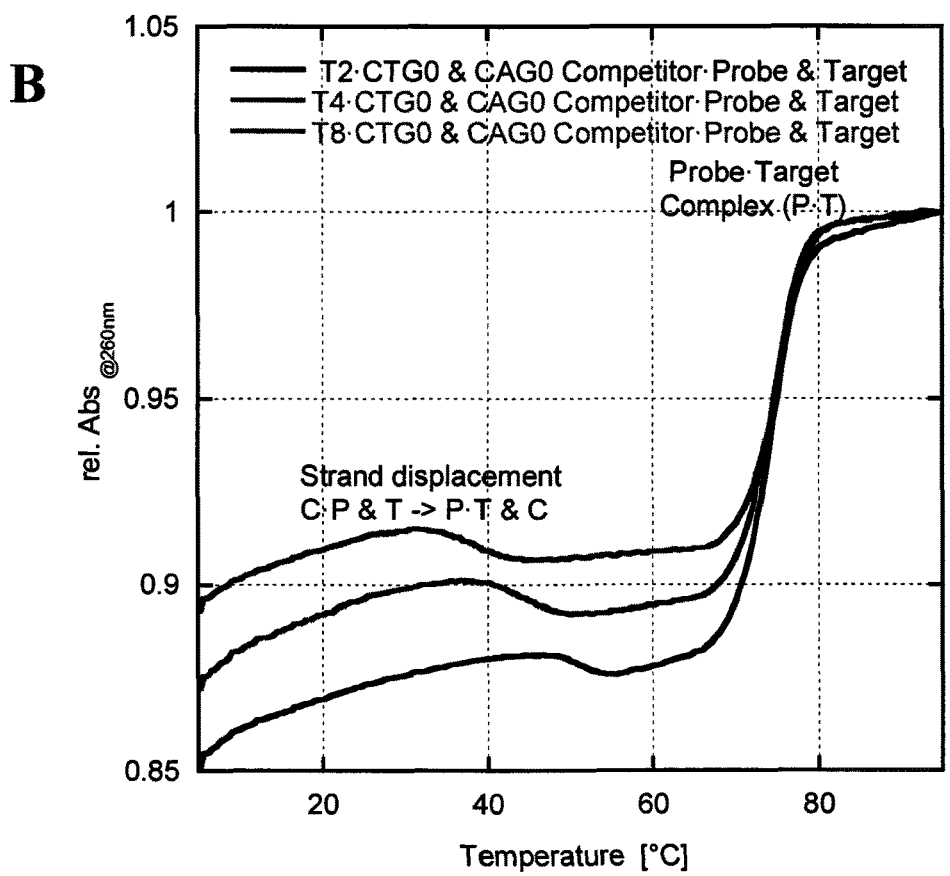

Here, spectroscopic and calorimetric techniques were used to demonstrate proof of principle for this methodology. It is shown in solution that energetically tuned probe complexes (C*P) not only can selectively detect the presence of target sequences, but also can quantitate the amount of target present. Specifically, a strand displacement reaction was conducted and monitored by optical methods using the all-T bulge loops (composed of a strand with variable length T loops and a 22 mer) as Competitor probe complex and the complementary 22 mer as single strand target (see FIG. 6). Notably, the temperature at which the competitor becomes displaced by the Target strand decreases with decreasing thermal stability of the probe competitor complex, i.e. T8 is displaced prior to T4 and T2 (see FIG. 7). Thus, the more the probe competitor complex is destabilized by increasing the loop size in the competitor strand, the lower the temperature at which strand exchange occurs. In other words, the system can be tuned in a way that yields the resolution and specificity desired. The thermal stability of the resulting probe-target complex is not affected by the presence or nature of the competitor (C*) strand.

Figure 8:
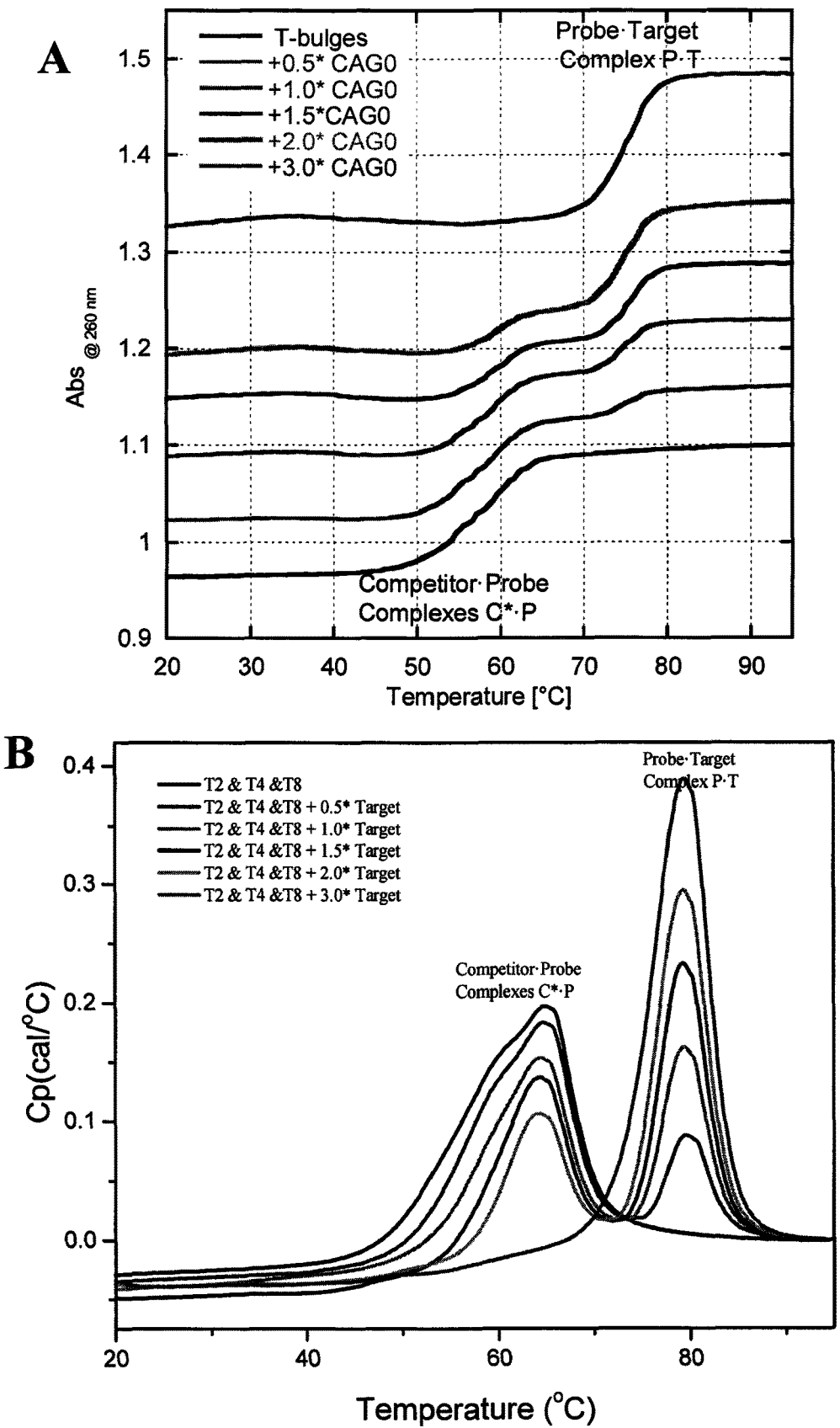
FIG. 8A shows UV melting curves and FIG. 8B provides the corresponding differential scanning calorimetry (DSC) melting curves of an equimolar mixture of T2•P, T4•P, and T8•P competitor•probe complexes in which the thermal stability of the (C*•P) is systematically modulated by the presence of "recognition neutral" T-bulges of increasing size (T2, T4, T8) upon addition of increasing amounts of Target strand T.

Additional optical and calorimetric data shown in FIG. 8 further demonstrate proof of principle of this next generation methodology. The crucial observation is the sequential disappearance of the low temperature segment of the composite T2•P, T4•P, and T8•P melting curve and the simultaneous appearance and increase in the P•T melting transition with increasing Target T concentration. As Target strand concentration increases, the thermally least stable component of the T2•P, T4•P, and T8•P mixture (T8•P, first then T4•P) undergoes strand exchange and consequently disappears from the composite melting curve, while the more stable components (primarily T2•P) remains unchanged.

Several publications and patent documents are cited throughout the specification in order to describe aspects of the present invention. Each of these references is incorporated herein as though set forth in full.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A population of two or more distinct molecular constructs capable of differentiating a target molecule from an off-target molecule and determining the target molecule concentration, said target molecule having a target domain and said off-target molecule having an off-target domain that differs from said target domain, each molecular construct comprising a distinct hybrid of
   a) a first domain that is capable of binding to said target domain and to said off-target domain, and
   b) a second domain that is at least partially hybridizable to said first domain,
   wherein the first domain of each molecular construct of the population is identical;
   wherein the free energy of displacement of the second domain from the first domain of the molecular construct by said target domain differs for each distinct molecular construct;
   wherein for each distinct molecular construct the free energy of displacement of the second domain from the first domain by said target domain is more favorable than the free energy of displacement of the second domain from the first domain by the off-target domain;

wherein the second domain of each molecular construct of said population of molecular constructs comprises a first subdomain that is at least partially complementary to the first domain and a second subdomain that is not complementary to the first domain;

wherein the second subdomain of each molecular construct modulates the binding of the first domain to the second domain of each molecular construct; and wherein the second subdomain of the second domain of each molecular construct forms a G-tetraplex.

2. The population of claim 1, wherein said off-target domain is generally homologous with respect to said target domain.

3. The population of claim 1, wherein said off-target domain differs from said target domain either chemically by at least one functional group or conformationally or both.

4. The population of claim 1, wherein said population comprises:
   a) a first subpopulation comprising at least one said molecular construct with respect to a first off-target domain and
   b) a second subpopulation comprising at least one said molecular construct with respect to a second off-target domain, and
   wherein said first off-target domain differs from said second off-target domain.

5. The population of claim 4, wherein said first off-target domain and said second off-target domain are disposed on the same off-target molecule.

6. The population of claim 4, wherein said first off-target domain and said second off-target domain are disposed on different off-target molecules.

7. The population of claim 4, wherein said first off-target domain is a target domain with respect to a second off-target molecule.

8. The population of claim 1, wherein the first and second domains of each molecular construct are attached to a solid support.

9. The population of claim 1, wherein each molecular construct is a nucleic acid molecule.

10. An array comprising more than one biosensor element on a solid support, wherein each biosensor element comprises a distinct molecular construct from the population of two or more distinct molecular constructs recited in claim 1.

11. A kit comprising at least one population of molecular constructs of claim 1.

12. An array of a plurality of populations in accordance with claim 1 for identifying a plurality of different target molecules in a sample and determining the relative number of each of those different target molecules in the sample, wherein the free energy of displacement from a molecular construct of one population for a target molecule is distinct from the free energy of displacement of other molecular constructs of the same or of another population for the same target molecule or for any other target molecule, such that each different target molecule in said sample can be identified, and the relative number of each of the different target molecules in said sample can be determined.

13. The array of claim 12, wherein the number of different targets is from about 2 to 10.

14. The array of claim 12, wherein the number of different targets is from 100 to 1000.

15. The array of claim 12, wherein the number of different targets is greater than 1000.

16. An array of two or more populations in accordance with claim 1, wherein the first domain of each molecular construct of a population is distinct from the first domain of each molecular construct of another population.

17. The array of claim 16, wherein the target domain which binds the first domain of the molecular constructs of a population is disposed on the same target molecule as the target domain which binds the first domains of the molecular constructs of another population.

18. The array of claim 16, wherein the target domain which binds the first domain of the molecular constructs of a population is an off-target domain for the first domain of the molecular construct of another population.

19. A method for differentiating a target molecule from an off-target molecule, said method comprising contacting the population of molecular constructs of claim 1 with an unknown molecule.

* * * * *

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Probe

<400> SEQUENCE: 1
tatgtatgct ttggtctttc tg    22

<210> SEQ ID NO 2
<211> LENGTH: 25
<212> TYPE: DNA
<213> ORGANISM: Artificial Sequence
<220> FEATURE:
<223> OTHER INFORMATION: Probe

<400> SEQUENCE: 2
gggttatggc gtgttggctg gagtg    25

<210> SEQ ID NO 3
<211> LENGTH: 27
<212> TYPE: DNA
<213> ORGANISM: Artificial Sequence
<220> FEATURE:
<223> OTHER INFORMATION: Competitor Strand

<400> SEQUENCE: 3
atacatacgt tttttttca gaaagac    27

<210> SEQ ID NO 4
<211> LENGTH: 21
<212> TYPE: DNA
<213> ORGANISM: Artificial Sequence
<220> FEATURE:
<223> OTHER INFORMATION: Competitor Strand

<400> SEQUENCE: 4
atacatacgt tccagaaaga c    21

<210> SEQ ID NO 5
<211> LENGTH: 22
<212> TYPE: DNA
<213> ORGANISM: Artificial Sequence
<220> FEATURE:
<223> OTHER INFORMATION: Competitor Strand

<400> SEQUENCE: 5
atacatacga aaccagaaag ac    22

<210> SEQ ID NO 6
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 6
tgcagaaaga ccaaagcata catattgaaa    30

<210> SEQ ID NO 7
<211> LENGTH: 27
<212> TYPE: DNA
<213> ORGANISM: Artificial Sequence

```
<220> FEATURE:
<223> OTHER INFORMATION: Probe

<400> SEQUENCE: 7
ttcaatatgt atgctttggt ctttctg                                              27

<210> SEQ ID NO 8
<211> LENGTH: 21
<212> TYPE: DNA
<213> ORGANISM: Artificial Sequence
<220> FEATURE:
<223> OTHER INFORMATION: Probe

<400> SEQUENCE: 8
cgagctgacg acarccatgc a                                                    21

<210> SEQ ID NO 9
<211> LENGTH: 21
<212> TYPE: DNA
<213> ORGANISM: Artificial Sequence
<220> FEATURE:
<223> OTHER INFORMATION: Probe

<400> SEQUENCE: 9
cttaccaaat cttgacatcc t                                                    21

<210> SEQ ID NO 10
<211> LENGTH: 21
<212> TYPE: DNA
<213> ORGANISM: Artificial Sequence
<220> FEATURE:
<223> OTHER INFORMATION: Probe

<400> SEQUENCE: 10
ttgttgagct tcatcgtgtt g                                                    21

<210> SEQ ID NO 11
<211> LENGTH: 40
<212> TYPE: DNA
<213> ORGANISM: Artificial Sequence
<220> FEATURE:
<223> OTHER INFORMATION: Competitor Strand

<400> SEQUENCE: 11
cacgagcacg ctttttttttt ttttttttttc acaccgaagc                              40

<210> SEQ ID NO 12
<211> LENGTH: 22
<212> TYPE: DNA
<213> ORGANISM: Artificial Sequence
<220> FEATURE:
<223> OTHER INFORMATION: Probe

<400> SEQUENCE: 12
gcttcggtgt ggcgtgctcg tg                                                   22
```